(12) United States Patent
Mahalingam et al.

(10) Patent No.: US 11,638,718 B2
(45) Date of Patent: May 2, 2023

(54) TREATMENT OF ALPHAVIRUS-INDUCED INFLAMMATION

(71) Applicant: GRIFFITH UNIVERSITY, Nathan (AU)

(72) Inventors: Surendran Mahalingam, Arundel (AU); Lara Josefina Herrero, Southport (AU)

(73) Assignee: Paradigm Biopharmaceuticals Limited, Melbourne (AU)

(*) Notice: Subject to any disclaimer, the term of this patent is extended or adjusted under 35 U.S.C. 154(b) by 7 days.

(21) Appl. No.: 16/884,628

(22) Filed: May 27, 2020

(65) Prior Publication Data
US 2021/0023124 A1 Jan. 28, 2021

Related U.S. Application Data

(63) Continuation of application No. 16/304,550, filed as application No. PCT/AU2016/050408 on May 26, 2016, now abandoned.

(51) Int. Cl.
| | | |
|---|---|---|
| A61K 31/737 | (2006.01) | |
| A61P 19/02 | (2006.01) | |
| A61P 31/14 | (2006.01) | |
| A61P 29/00 | (2006.01) | |
| A61K 9/00 | (2006.01) | |

(52) U.S. Cl.
CPC .......... *A61K 31/737* (2013.01); *A61K 9/0019* (2013.01); *A61P 19/02* (2018.01); *A61P 29/00* (2018.01); *A61P 31/14* (2018.01); *Y02A 50/30* (2018.01)

(58) Field of Classification Search
CPC ..... A61K 31/737; A61K 9/0019; A61P 19/02; A61P 29/00; A61P 31/14
See application file for complete search history.

(56) References Cited

U.S. PATENT DOCUMENTS

| | | | | |
|---|---|---|---|---|
| 5,288,704 A | * | 2/1994 | Ungheri | A61P 31/16 514/59 |
| 2003/0181416 A1 | * | 9/2003 | Comper | A61P 31/14 514/56 |
| 2016/0145323 A1 | * | 5/2016 | Doranz | C07K 16/1081 530/389.4 |

FOREIGN PATENT DOCUMENTS

| | | |
|---|---|---|
| WO | WO 88/07060 A1 | 9/1988 |
| WO | WO 2012027797 A1 | 3/2012 |

OTHER PUBLICATIONS

Baba, M., Snoeck, R., Pauwels, R., & De Clercq, E. (1988). Sulfated polysaccharides are potent and selective inhibitors of various enveloped viruses . . . Antimicrobial agents and chemotherapy, 32(11), 1742-1745. (Year: 1988).*

Mbazima, V., Dias, B. D. C., Omar, A., Jovanovic, K., & Weiss, S. F. (2010). Interactions between PrPc and other ligands with the 37-kDa/67-kDa laminin receptor. Frontiers in Bioscience-Landmark, 15(3), 1150-1163. (Year: 2010).*

Pardigon, N. (2009). The biology of chikungunya: a brief review of what we still do not know. Pathologie Biologie, 57(2), 127-132. (Year: 2009).*

Burt et al.; "Chikungunya: A Re-Emerging Virus;" Lancet; (Feb. 18, 2012); pp. 662-671; vol. 379; <doi: 10.1016/S0140-6736(11)60281-X>.

Noël et al.; "Spread of Chikungunya from the Caribbean to Mainland Central and South America: A Greater Risk of Spillover in Europe?;" Eurosurveillance; (Jul. 17, 2014); 3 pages: pii=20855; vol. 19, No. 28.

Centers for Disease Control and Prevention; "First Chikungunya Case Acquired in the United States Reported in Florida;" (Jul. 17, 2014); 3 pages; <URL: https://www.cdc.gov/media/releases/2014/p0717-chikungunya.html>.

Pan American Health Organization; "Chikungunya;" 1 page.

Herrero et al.; "Applications of Animal Models of Infectious Arthritis in Drug Discovery: A Focus on Alphaviral Disease;" Current Drug Targets; (2011); pp. 1024-1036; vol. 12, No. 7.

Manimunda et al.; "Clinical Progression of Chikungunya Fever During Acute and Chronic Arthritic Stages and the Changes in Joint Morphology as Revealed by Imaging;" Transactions of the Royal Society of Tropical Medicine and Hygiene; (2010); pp. 392-399; vol. 104; <doi: 10.1016/j.trstmh.2010.01.011>.

Fraser et al.; "Cytology of Synovial Effusions in Epidemic Polyarthritis;" Australian and New Zealand Journal of Medicine; (Apr. 1981); pp. 168-173; vol. 11.

Fraser et al.; "The Exanthem of Ross River Virus Infection: Histology, Location of Virus Antigen and Nature of Inflammatory Infiltrate;" Journal of Clinical Pathology; (1983); pp. 1256-1263; vol. 36.

Soden et al.; "Detection of Viral Ribonucleic Acid and Histologic Analysis of Inflamed Synovium in Ross River Virus Infection;" Arthritis & Rheumatism; (Feb. 2000); pp. 365-369; vol. 43, No. 2.

Herrero et al.; "Macrophage Migration Inhibitory Factor Receptor CD74 Mediates Alphavirus-Induced Arthritis and Myositis in Murine Models of Alphavirus Infection;" Arthritis & Rheumatism; (Oct. 2013); pp. 2724-2736; vol. 65, No. 10; <doi: 10.1002/art.38090>.

Herrero et al. "Critical Role for Macrophage Migration Inhibitory Factor (MIF) in Ross River Virus-Induced Arthritis and Myositis;" Proceedings of the National Academy of Sciences of the United States of America; (Jul. 19, 2011); pp. 12048-12053; vol. 108, No. 29; <doi: 10.1073/pnas.1101089108>.

(Continued)

*Primary Examiner* — Dale R Miller
(74) *Attorney, Agent, or Firm* — Thorpe North & Western, LLP

(57) ABSTRACT

Disclose is a method of treating alphavirus infections, particularly in humans, in which pentosan polysulfate is administered to an infected subject. Whilst not effecting the viral load in a subject, the pentosan polysulfate acts to reduce inflammation in tissues, such as the muscles, and in the joints of a subject. In addition, cartilage damage in the joints may be reduced. The reduction in inflammation and/or cartilage damage acts to reduce the severe pain experienced by subjects suffering from alphavirus infections, such as Ross River virus, chikungunya virus and Barmah Forest virus.

13 Claims, 8 Drawing Sheets
Specification includes a Sequence Listing.

(56) References Cited

OTHER PUBLICATIONS

Nakaya et al.; "Gene Profiling of Chikungunya Virus Arthritis in a Mouse Model Reveals Significant Overlap with Rheumatoid Arthritis;" Arthritis & Rheumatism; (Nov. 2012); pp. 3553-3563; vol. 64, No. 11; <doi: 10.1002/art.34631 >.
Bresnihan; "Pathogenesis of Joint Damage in Rheumatoid Arthritis;" In: Proceedings of the OMERACT IV Conference; (OMERACT IV 1998); 3 pages; Part3: Rheumatoid Arthritis: Imaging.
Otero et al.; "Cells of the Synovium in Rheumatoid Arthritis: Chondrocytes;" Arthritis Research & Therapy; (2007); 13 pages; vol. 9, No. 220; <doi: 10.1186/ar2292 >.
Parsons et al.; "Successful Therapy of Interstitial Cystitis with Pentosanpolysulfate;" The Journal of Urology; (Sep. 1987); pp. 513-516; vol. 138.
Kumagai et al.; "Sodium Pentosan Polysulfate Resulted in Cartilage Improvement in Knee Osteoarthritis—An Open Clinical Trial;" BMC Clinical Pharmacology; (2010); 9 pages; vol. 10, No. 7.
Ghosh et al.; "Effects of Pentosan Polysulfate in Osteoarthritis of the Knee: A Randomized, Double-Blind, Placebo-Controlled Pilot Study;" Current therapeutic Research; (Nov./Dec. 2005); pp. 552-571; vol. 66, No. 6; <doi: 10.1016/j.curtheres.2005.12.012 >.
Ghosh; "The Pathobiology of Osteoarthritis and the Rationale for the Use of Pentosan Polysulfate for Its Treatment;" Seminars in Arthritis and Rheumatism; (Feb. 1999); pp. 211-267; vol. 28, No. 4.
Kongtawelert et al.; "Pentosan Polysulfate (Cartrophen®) Prevents the Hydrocortisone Induced Loss of Hyaluronic Acid and Proteoglycans from Cartilage of Rabbit Joints as Well as Normalizes the Keratan Sulfate Levels in Their Serum;" The Journal of Rheumatology; (1989); pp. 1454-1459; vol. 16, No. 11.
Kuhn et al.; "Infectious RNA Transcripts from Ross River Virus cDNA Clones and the Construction and Characterization of Defined Chimeras with Sindbis Virus;" Virology; (1991); pp. 430-441; vol. 182.
Lidbury et al.; "Macrophage-Induced Muscle Pathology Results in Mobidity and Mortality for Ross River Virus-Infected Mice;" The Journal of Infectious Diseases; (2000); pp. 27-34; vol. 181, No. 27.
Morrison et al.; "Characterization of Ross River Virus Tropism and Virus-Induced Inflammation in a Mouse model of Viral Arthritis and Myositis;" Journal of Virology; (Jan. 2006); pp. 737-749; vol. 80, No. 2; <doi: 10.1128/JVI.80.2.737-749.2006 >.
Bachmanov et al.; "Food Intake, Water Intake, and Drinking Spout Side Preference of 28 Mouse Strains;" Behavior Genetics; (Nov. 2002); pp. 435-443; vol. 32, No. 6.
Reagan-Shaw et al.; "Dose Translation from Animal to Human Studies Revisited;" Federation of American Societies for Experimental Biology Journal; Life Sciences Forum; (Mar. 2007); pp. 659-661; vol. 22.
Glasson et al.; "The OARSI Histopathology Initiative—Recommendations for Histological Assessments of Osteoarthritis in the Mouse;" Osteoarthritis and Cartilage; (2010); S17-S23; vol. 18; <doi: 10.1016/j.joca.2010.05.025 >.
Shabman et al.; "Ross River Virus Envelope Glycans Contribute to Type I Interferon Production in Myeloid Dendritic Cells;" Journal of Virology; (Dec. 2008); p. 12374-12383; vol. 82, No. 24; <doi: 10.1128/JVI.00985-08 >.
Camplejohn et al.; "Limitations of Safranin 'O' Staining in Proteoglycan-Depleted Cartilage Demonstrated with Monoclonal Antibodies;" Histochemistry; (1988); pp. 185-188; vol. 89.
Gunn et al.; "Mannose Binding Lectin is Required for Alphavirus-Induced Arthritis/Myositis;" PLoS Pathogens; (Mar. 2012); 14 pages; vol. 8, Issue 3; <doi: 10.1371/journal.ppat.1002586 >.
Lidbury et al.; "Macrophage-Derived Proinflammatory Factors Contribute to the Development of Arthritis and Myositis after Infection with an Arthrogenic Alphavirus;" The Journal of Infectious Diseases; (2008); pp. 1585-1593; vol. 197; <doi: 10.1086/587841 >.
Javier et al.; "Bindarit, An Inhibitor of Monocyte Chemotactic Protein Synthesis, Protects against Bone Loss Induced by Chikungunya Virus Infection;" Journal of Virology; (2015); <doi: 10.1128/JVI.02034-14 >.

Chen et al.; "Arthritogenic Alphaviral Infection Perturbs Osteoblast Function and Triggers Pathologic Bone Loss;" Proceedings of the National Academy of Sciences of the United States of America; (Apr. 22, 2014); pp. 6040-6045; vol. III, No. 16; <doi: 10.1073/pnas.l318859111 >.
Chen et al.; "Arthritogenic Alphaviruses: New Insights into Arthritis and Bone Pathology;" Trends in Microbiology; (Jan. 2015); pp. 35-43; vol. 23, No. 1; <doi: 10.1016/j.tim.2014.09.005 >.
Mann et al.; "Aberrant Repair and Fibrosis Development in Skeletal Muscle;" Skeletal Muscle; (2011); 20 pages; vol. 1, No. 21.
Morrison et al.; "Complement Contributes to Inflammatory Tissue Destruction in a Mouse Model of Ross River virus-Induced Disease;" Journal of Virology; (May 2007); pp. 5132-5143; vol. 81, No. 10; <doi: 10.1128/JVI.02799-06 >.
Ma et al.; "The Role of Macrophages in Rheumatoid Arthritis;" Current Pharmaceutical Design; (Feb. 2005); pp. 569-580; vol. 11, No. 5.
Poo et al.; "CCR2 Deficiency Promotes Exacerbated Chronic Erosive Neutrophil-Dominated Chikungunya Virus Arthritis;" Journal of Virology; (2014); pp. 6862-6872; <doi: 10.1128/JVI.033364-13 >.
Seeberger et al.; "Glycans in Biotechnology and the Pharmaceutical Industry;" Essentials of Glycobiology; (2017); Chapter 57, $3^{rd}$ Edition; <doi: 10.1101/glycobiology.3e.057 >.
Varki; "Glycan-Based Interactions Involving Vertebrate Sialic-Acid-Recognizing Proteins;" Nature; (Apr. 26, 2007); vol. 446; <doi: 10.1038/nature05816 >.
Nickel et al.; "Randomized, Double-Blind, Dose-Ranging Study of Pentosan Polysulfate Sodium for Interstitial Cystitis;" Urology; (2005); pp. 654-658; vol. 65; <doi: 10.1016/j.urology.2004.10.071 >.
Maffrand et al.; "Experimental and Clinical Pharmacology of Pentosan Polysulfate;" Seminars in Thrombosis and Hemostasis; (1991); pp. 186-198; vol. 17, Supplement 2.
Wu et al.; "Inhibition of Inflammation by Pentosan Polysulfate Impedes the Development and Progression of Severe Diabetic Nephropathy in Aging C57B6 Mice;" Laboratory Investigation; (Oct. 2011); pp. 1459-1471; vol. 91; <doi: 10.1038/labinvest.2011.93 >.
Stoermer et al.; "Genetic Ablation of Arginase 1 in Macrophages and Neutrophils Enhances Clearance of an Arthritogenic Alphavirus;" The Journal of Immunology; (Sep. 12, 2012); pp. 4047-4059; vol. 189; <doi: 10.4049/jimmunol.1201240 >.
Deng et al.; "IL-10 Triggers Changes in Macrophage Phenotype That Promote Muscle Growth and Regeneration;" The Journal of Immunology; (Aug. 29, 20212); pp. 3669-3680; vol. 189; <doi: 10.4049/jimmunol.1103180 >.
Arnold et al.; "Inflammatory Monocytes Recruited after Skeletal Muscle Injury Switch into Antiinflammatory Macrophages to Support Myogenesis;" The Journal of Experimental Medicine; (May 14, 2007); pp. 1057-1069; vol. 204, No. 5; <doi: 10.1084/jem.20070075 >.
Couper et al.; "IL-10: The Master Regulator of Immunity to Infection;" The Journal of Immunology; (2008); pp. 5771-5777; vol. 180; <doi: 10.4049/jimmunol.180.9.5771 >.
Kilgore et al.; "The Semisynthetic Polysaccharide Pentosan Polysulfate Prevents Complement-Mediated Myocardial Injury in the Rabbit Perfused Heart;" The Journal of Pharmacology and Experimental Therapeutics; (Feb. 16, 1998); pp. 987-994; vol. 285, No. 3.
Smith et al.; "The Effects of Orally Administered Calcium Pentosan Polysulfate on Inflammation and Cartilage Degradation Produced in Rabbit Joints by Intraarticular Injection of a Hyaluronate-Polylysine Complex;" Arthritis & Rheumatism; (Jan. 1994); pp. 125-136; vol. 37, No. 1.
Morrison et al.; "Dominant Negative MCP-1 Blocks Human Osteoclast Differentiation;" Journal of Cellular Biochemistry; (2014); pp. 303-312; vol. 115; <doi: 10.1002/jcb.24663 >.
Takizawa et al.; "Calcium Pentosan Polysulfate Directly Inhibits Enzymatic Activity of ADAMTS4 (Aggrecanase-1) in Osteoarthritic Chondrocytes;" Federation of European Biochemical Societies; (Jul. 29, 2008); pp. 2945-2949; vol. 582; <doi: 10.1016/j.febslet.2008.07.036 >.

(56) References Cited

OTHER PUBLICATIONS

Ghosh et al.; "Pentosan Polysulfate Promotes Proliferation and Chondrogenic Differentiation of Adult Human Bone Marrow-Derived Mesenchymal Precursor Cells;" Arthritis Research & Therapy; (2010); 17 pages; vol. 12:R28.

Kramer et al.; "Survey of the Therapeutic Approach and Efficacy of Pentosan Polysulfate for the Prevention and Treatment of Equine Osteoarthritis in Veterinary Practice in Australia;" The Journal of the Australian Veterinary Association LTD; (2014); pp. 482-487; vol. 92; <doi: 10.1111/avj.12266>.

Troeberg et al.; "Calcium Pentosan Polysulfate is a Multifaceted Exosite Inhibitor of Aggrecanases;" The Journal of the Federation of American Societies for Experimental Biology; (Oct. 2008); pp. 3515-3524; vol. 10; <doi: 10.1096/fj.08-112680>.

Al-Zahrani et al.; "Long-Term Efficacy and Tolerability of Pentosan Polysulphate Sodium in the Treatment of Bladder Pain Syndrome;" Canadian Urological Asssociation Journal; (2011); pp. 113-118; vol. 5, No. 2; <doi: 10.5489/cuaj.10095>.

Bancos et al.; "Ibuprofen and Other Widely used Non-steroidal Anti-Inflammatory Drugs Inhibit Antibody Production in Human Cells;" Cellular Immunology; (2009); pp. 18-28; vol. 258; <doi: 10.1016/j.cellimm.2009.03.007>.

Rulli et al.; "Amelioration of Alphavirus-Induced Arthritis and Myositis in a Mouse Model by Treatment with Bindarit, an Inhibitor of Monocyte Chemotactic Proteins;" Arthritis & Rheumatism; (Aug. 2009); pp. 2513-2523; vol. 60, No. 8; <doi: 10.1002/art.24682>.

Zaid et al.; "Exacerbation of Alphaviral Arthritis and Myositis in a Mouse Model after Etanercept Treatment is Due to Diminished Levels of Interferon $\alpha/\beta$;" Virology & Mycology; (2013); 2 pages; vol. 2, Issue 3; <doi: 10.4172/2161-0517.1000122>.

Taylor et al.; Methotrexate Treatment Causes Early Onset of Disease in a Mouse Model of Ross River Virus-Induced Inflammatory Disease Through Increased Monocyte Production; PLoS One; (Aug. 12, 2013); 7 pages; vol. 8.8; <doi: 10.1371/journal.pone.0071146>.

Herrero et al.; "Pentosan Poly sulfate: A Novel Glycosaminoglycan-Like Molecule for Effective Treatment of Alphavirus-Induced Cartilage Destruction and Inflammatory Disease;" Journal of Virology; (Aug. 2015); pp. 8063-8076; vol. 89, No. 15; <doi: 10.1128/JVI.00224-15>.

Assuncao-Miranda et al.; "Molecular Mechanisms Involved in the Pathogenesis of Alphavirus-Induced Arthritis;" BioMed Research International; (Aug. 2013); 11 pages; vol. 2013, Article ID 973516; <doi: 10.1155/2013/973516>.

Lui et al.; "Polyarthritis in Four Patients with Chikungunya Arthritis;" Singapore Medical Journal; (2012); pp. 241-243; vol. 53, No. 4.

International Search Report dated Jul. 26, 2016, in International Application No. PCT/AU2016/050408, filed May 26, 2016; 4 pages.

Pan American Health Organization.; "Chikungunya." Retrieved from https://www.paho.org/en/topics/chikungunva 14 pages.

* cited by examiner

Figure 1
Knee joint
A  Mock Control      RRV
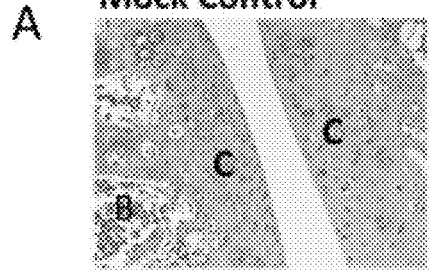 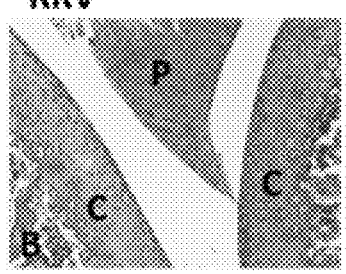
B
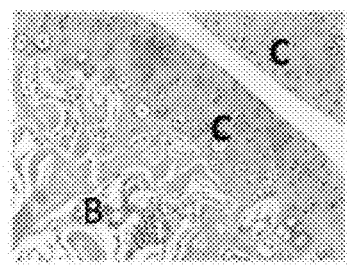 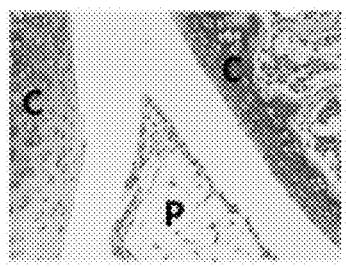
C
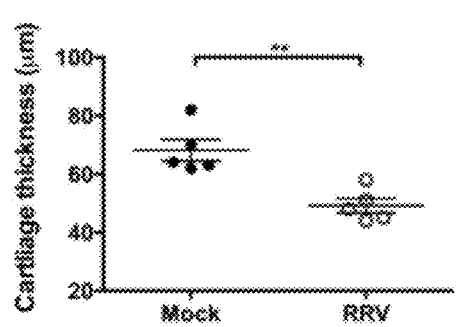 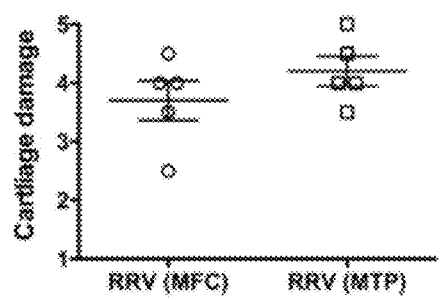
Di 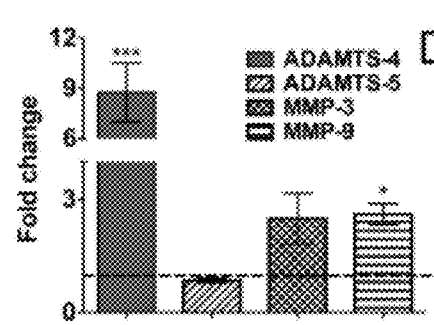 Dii 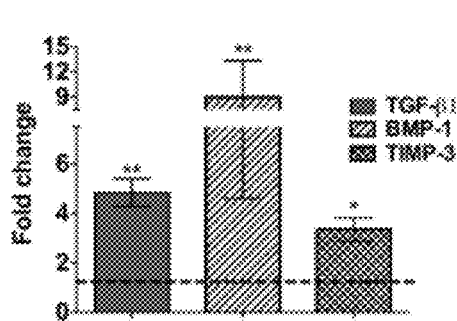

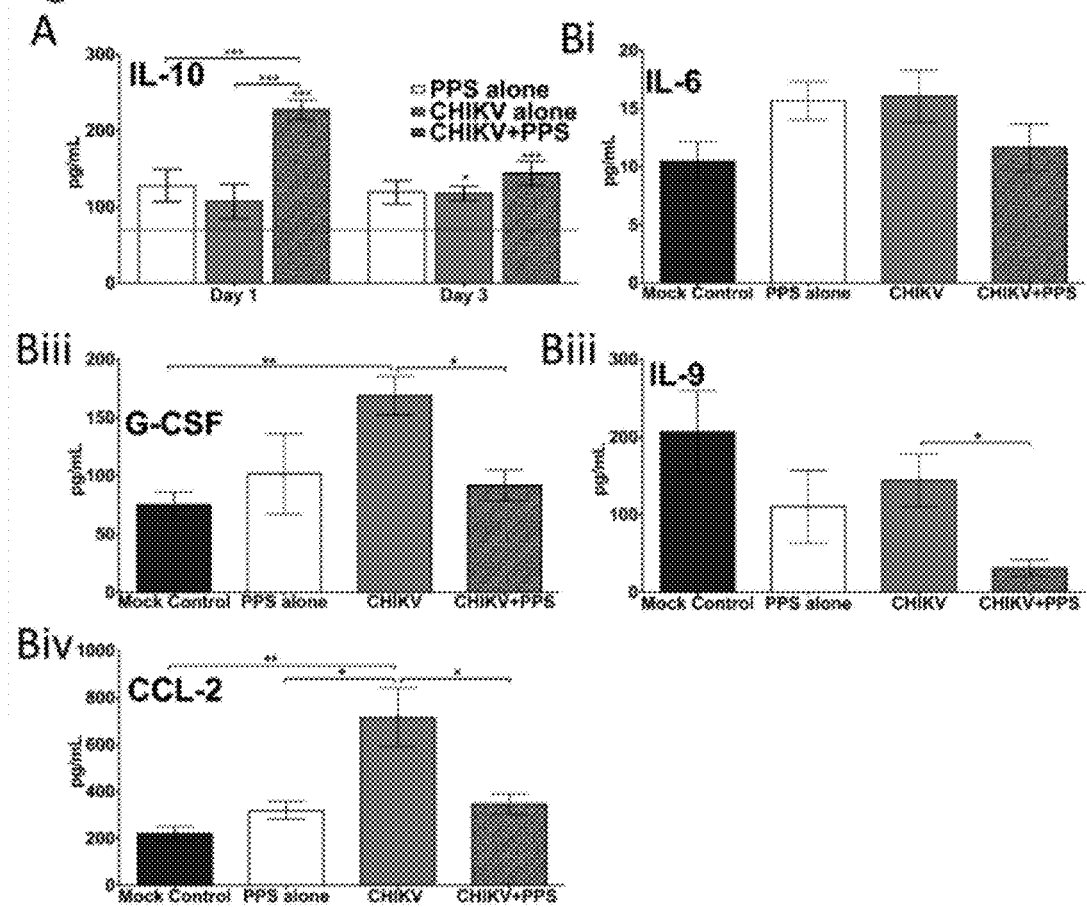

TREATMENT OF ALPHAVIRUS-INDUCED INFLAMMATION

The present application is a continuation of U.S. patent application Ser. No. 16/304,550, filed on Nov. 26, 2018, which was a U.S. National Stage Application under 35 U.S.C. 371 of PCT/AU2016/050408, filed on May 26, 2016, each of which is incorporated herein by reference.

TECHNICAL FIELD

This invention relates to the treatment of animals, especially humans, infected with alphaviruses and more particularly to a treatment directed to the reduction of inflammation and/or cartilage damage arising from the infection.

BACKGROUND

Arthropod-borne arthritogenic alphaviruses such as Ross River virus (RRV) and chikungunya virus (CHIKV) cause large epidemics of severe musculoskeletal disease. They have been progressively expanding their global distribution, regularly emerging in new regions of the world (1, 2). The hallmark of alphavirus disease is crippling joint pain and arthritis, which often has an extended duration leaving patients bed-ridden and incapacitated. In 2014-2015, CHIKV further expanded its global distribution by entering the Americas and is circulating in several Caribbean islands. As of $23^{rd}$ May 2016, the Pan American Health Organization (PAHO) reported an estimated total of over 1.5 million cases since 2014, with 100,000 reported in 2016 so far; additionally, the first report of local autochthonous CHIKV transmission in mainland USA was reported in July 2014 (3, 4). Due to the expanding range of alphaviral infections, understanding the mechanisms by which alphaviruses cause debilitating arthritic disease has become increasingly important, especially as there are no specific treatments available (5).

The severe arthralgia/arthritis in the joints caused by alphaviruses can be both acute and chronic. Ultrasonography of CHIKV patients with joint pain reveals striking tenosynovitis; bone erosion and synovial thickening (6). RRV antigen has been detected by immunofluorescence in synovial monocytes and macrophages during the early phase of illness (7), and in basal epidermal and eccrine duct epithelia three days after the onset of RRV exanthem (8). Using antigen staining and RT-PCR RRV has also been detected in synovial effusions more than one month after the onset of symptoms, providing evidence of persistent infection in the inflamed synovium (9).

The synovial space of joints is glycan-rich, containing high levels of glycosaminoglycan (GAGS) frequently linked to protein backbones that form proteoglycan structures. Chondrocytes are the major cell type producing the matrix of articular cartilage that is rich in proteoglycans (14). However, there have been no studies to elucidate the impact of alphaviruses on cartilage and the proteoglycan matrix of the joint.

In the work described herein, we show RRV infection results in similar histopathology of the joint to that observed in rheumatoid arthritis (RA). This includes pannus-like formation, immune infiltration and cartilage damage. We further show that treatment with pentosan polysulfate (PPS) ameliorates the severity of both RRV and CHIKV clinical disease, overall reduction in both immune infiltrates and soluble pro-inflammatory factors. We also observed a change in the kinetics of the soluble factors involved in macrophage activation. In RRV-infection treatment also reduced the loss of articular cartilage and protected the level of proteoglycans in the cartilage matrix, altering the expression of cartilage components including aggrecan (SEQ. ID. NO. 2) and collagen in. Overall we show that PPS is a safe and effective treatment for both acute and chronic RRV-infection.

SUMMARY

Accordingly the present invention consists in a method of treating a subject having an alphavirus infection comprising administering parenterally an amount of pentosan polysulfate or a salt thereof effective to reduce alphavirus induced inflammation and/or alphavirus induced cartilage damage in the subject.

In another aspect, the present invention consists in the use of pentosan polysulfate or a salt thereof in the preparation of a medicament for the treatment of alphavirus induced inflammation and/or to reduce alphavirus induced cartilage damage in a subject having an alphavirus infection.

In a further aspect, the present invention consists in a composition comprising pentosan polysulfate and a pharmaceutically acceptable carrier for use in treating alphavirus induced inflammation and/or to reducing alphavirus induced cartilage damage in a subject having an alphavirus infection.

Whilst the subject to be treated may be an animal, preferably the subject is a human infected with an alphavirus.

BRIEF DESCRIPTION OF DRAWINGS

FIG. 1. RRV-infection results in damages to the cartilage in joint tissues.

20-day-old C57BL/6 mice were infected s.c. With $10^4$ pfu RRV or mock-infected with diluent alone. Infection resulted in extensive inflammation, pannus formation, articular cartilage thinning, disruption of the proteoglycans and upregulation of cartilage associated genes. (A, B) For histological analysis the joints of RRV-infected mice were sacrificed at peak disease at 10 days p.i., perfused with 4% PFA, knee joint tissues removed, paraffin-embedded and 5 µm sections generated. Sections were stained with (A) H&E or (B) Safranin O/fast green. Annotations; (B) bone, (C) cartilage, (P) pannus. Images are representative of at least 5 mice per group (magnification 100×). (C) The width of cartilage from mock- and RRV-infected mice were measured in five areas per mouse and averaged with each point representing one mouse. Cartilage degradation from the medial femoral condyle (MFC) and the medial tibia plateau (MTP) of RRV mice was assessed as outlined in the methods, mock control mice show a score of 1. Data represent mean±SEM of 5 mice per group. (D) Similarly, at both early time points (i) and at peak disease (ii) total RNA from ankle joint tissues was isolated and analysed for mRNA expression by qRT-PCR. Data was normalised to the housekeeping gene HPRT1 and expressed as relative expression compared to mock-infected controls (as represented by the dashed line). Each bar represents the mean+/−the SEM for 5-6 mice per group, *$p<0.05$, ***$p<0.001$ one-way ANOVA. Dunnett's post test.

Figure 2:
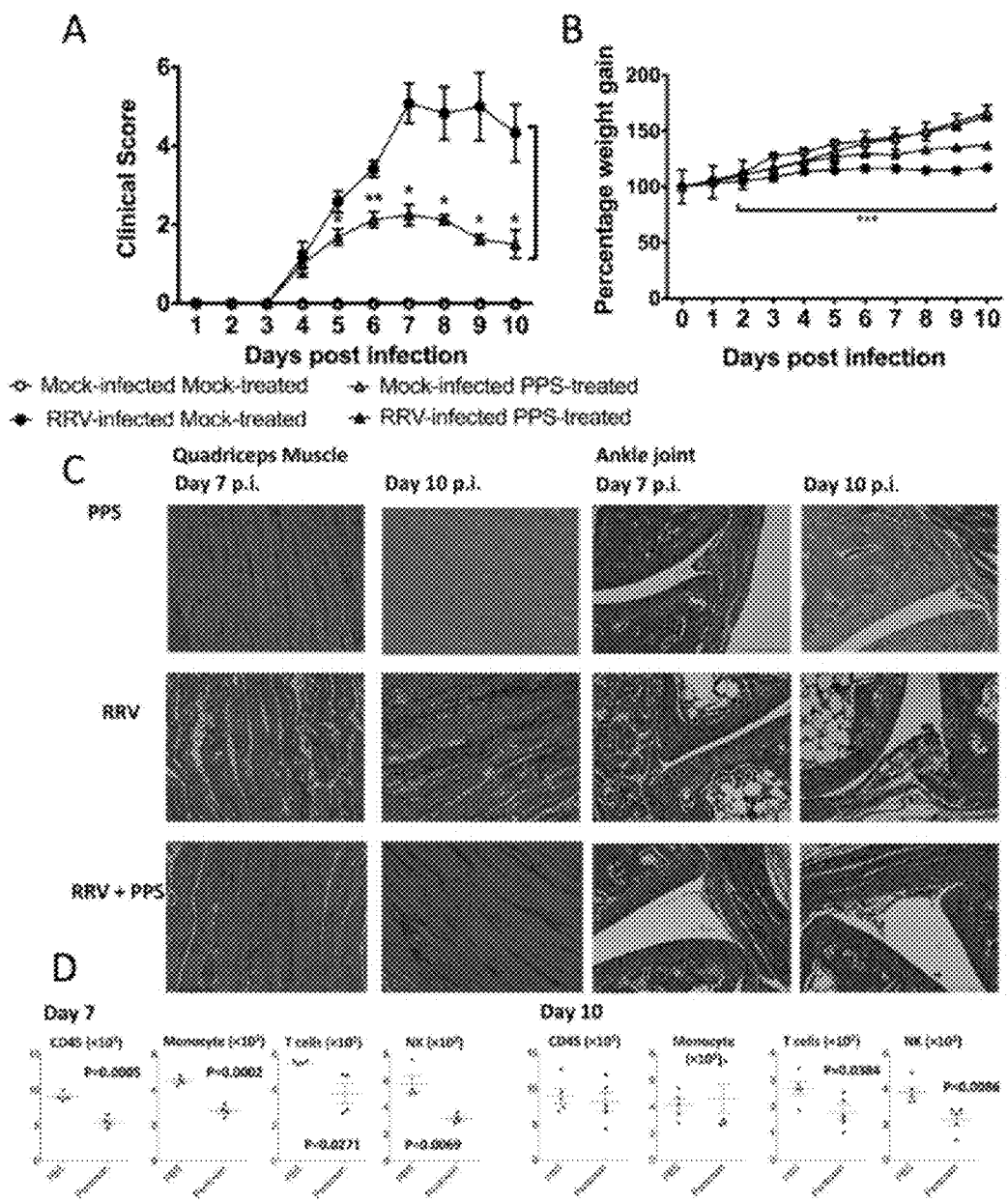

FIG. 2. Pentosan polysulfate reduces the severity of acute RRV-induced inflammatory disease.

PPS treatment reduced the level of disease signs, prevented severe weight loss and reduced the level of inflammatory infiltrates into the joint and muscle tissues protecting the muscle tissue from extensive RRV-induced damage. 20-day-old C57BL/6 mice were infected s.c. with $10^4$ pfu RRV or mock-infected with diluent alone then either treated daily i.p. with PPS at 3 mg/kg in 100 μL PBS or mock-treated with PBS alone. (A) Mice were scored for the development of hind-limb dysfunction and displayed a reduction in RRV-disease severity with PPS treatment. Mock-infected mice were scored zero for the duration of the experiment *p<0.05, p<0.01 using a Mann-Whitney test. (B) Weight was monitored at 24-hour intervals *p<0.001 significantly reduced weight loss of RRV-infected PPS-treated compared to RRV-infected mock-treated-using two-way ANOVA with Bonferroni post test. (C) For histological analysis, mice were sacrificed at 7 or 10 days p.i., perfused with 4% PFA, quadriceps and knee joint tissues removed, paraffin-embedded, 5 μm sections generated. Sections were stained with H&E. (D) Quadriceps muscles were removed from RRV-infected 'pentosan' and 'PBS' treated mice at day 7 and 10 p.i., cells were isolated, counted and stained for CD45, Gr1, CD11b, pan NK/NKT, CD3 and CD19 expression. Total leukocyte (CD45$^{hi}$), inflammatory monocyte (Gr1$^{hi}$CD11b$^{hi}$) NK/NKT (CD45$^{hi}$ pan NK$^{hi}$) and T cell (CD3$^{hi}$) populations were determined among total live (PI-negative) infiltrated cells using various gating strategies, analysed by Student t test. Each data point represents the mean+/−SEM of 5 to 10 mice and is representative of 3-4 independent experiments.

Figure 3:
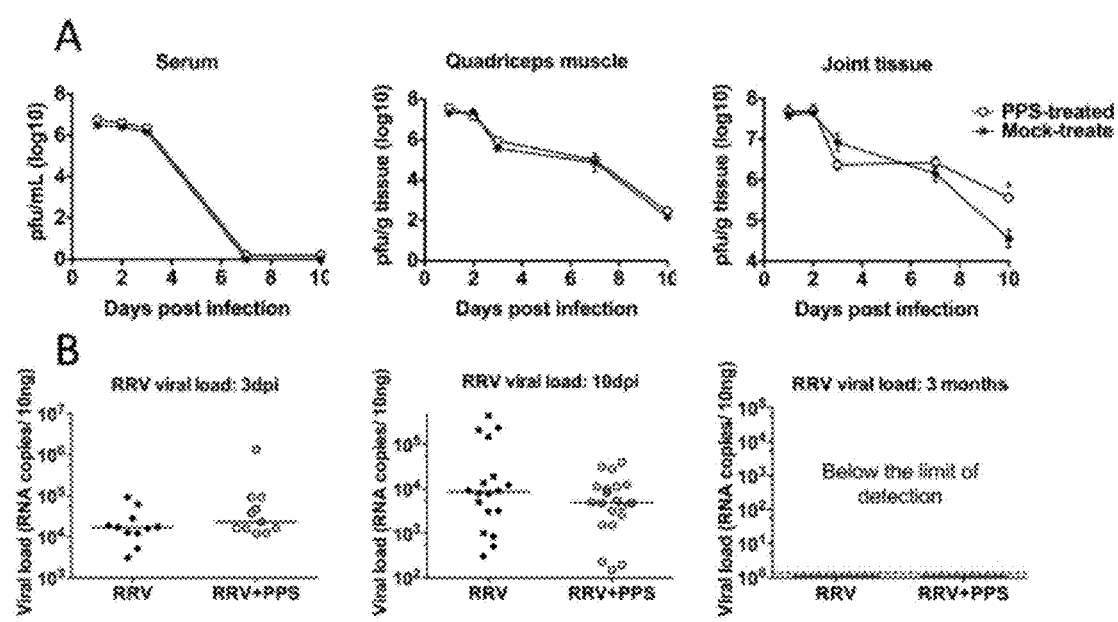

FIG. 3. PPS-treatment does not alter the kinetics of viral replication.

Both infectious virus and viral RNA levels were measured indicating PPS-treatment did not affect viral clearance, Mice were infected s.c. with RRV or mock-infected with diluent alone then either treated daily i.p. with PPS or mock-treated with PBS alone. At days 1, 2, 3, 7 and 10 p.i. the serum, quadriceps and ankle tissues were harvested, homogenised and the viral load determined by (A) plaque assay on Vero cells for infectious virus or (B) by qPCR for viral RNA with nsp3 specific primers using a standard generated from serial dilutions of RRV T48 infectious plasmid. Each data point represents a single mouse, line indicates the median value. *p<0.05 using two-way ANOVA with Bonferroni post test for plaque assay and unpaired Mann-Whitney for PCR.

Figure 4:
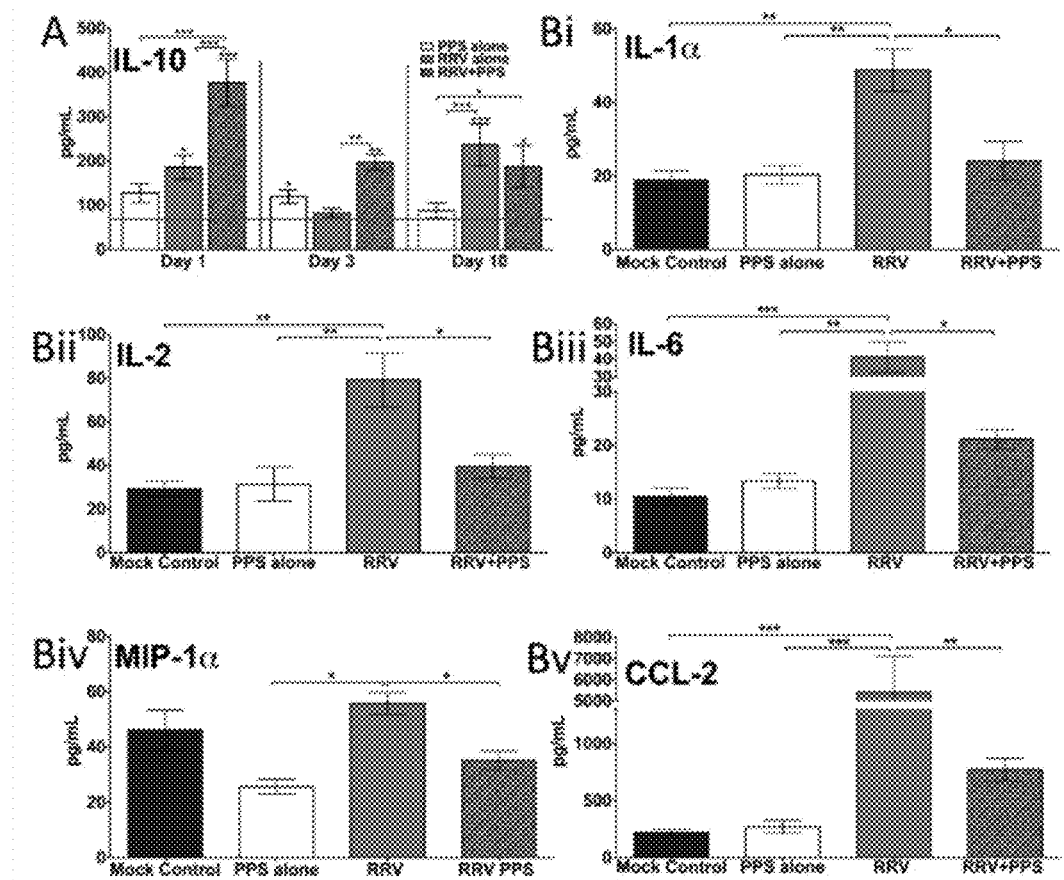

FIG. 4. PPS-treatment alters the expression of soluble factors in RRV-inflammatory disease.

20-day-old C57BL/6 mice were infected s.c. with $10^4$ pfu RRV or mock-infected with diluent alone then either treated daily i.p. with PPS at 3 mg/kg in 100 μL PBS or mock-treated with PBS alone (mock-infected mock-treated=Mock control, mock-infected PPS-treated=PPS alone, RRV-infected mock-treated=RRV alone. RRV-infected PPS-treated=RRV+PPS). At days 1, 3 and 10 p.i. serum was collected and analysed for level of soluble factors using Bio-Plex Pro Mouse Cytokine 23-plea kits (Biorad). (A) PPS treatment reduced the levels pro-inflammatory factors at day 10 p.i., (B) increased levels of chemo-attractants factors at day 1 p.i. and (C) altered the kinetics of M2 cytokine IL-10. Red line indicates the level of mock control. Each data point represents the mean+/−standard error of 5 to 6 mice. (A, B) *p<0.05, p<0.01,  *p<0.001 one-way ANOVA with Tukey's post test. (C) *p<0.05, p<0.01, *p<0.001 using two-way ANOVA with Bonferroni post test. Astrices directly on top of bars are compared to mock control levels.

Figure 5:
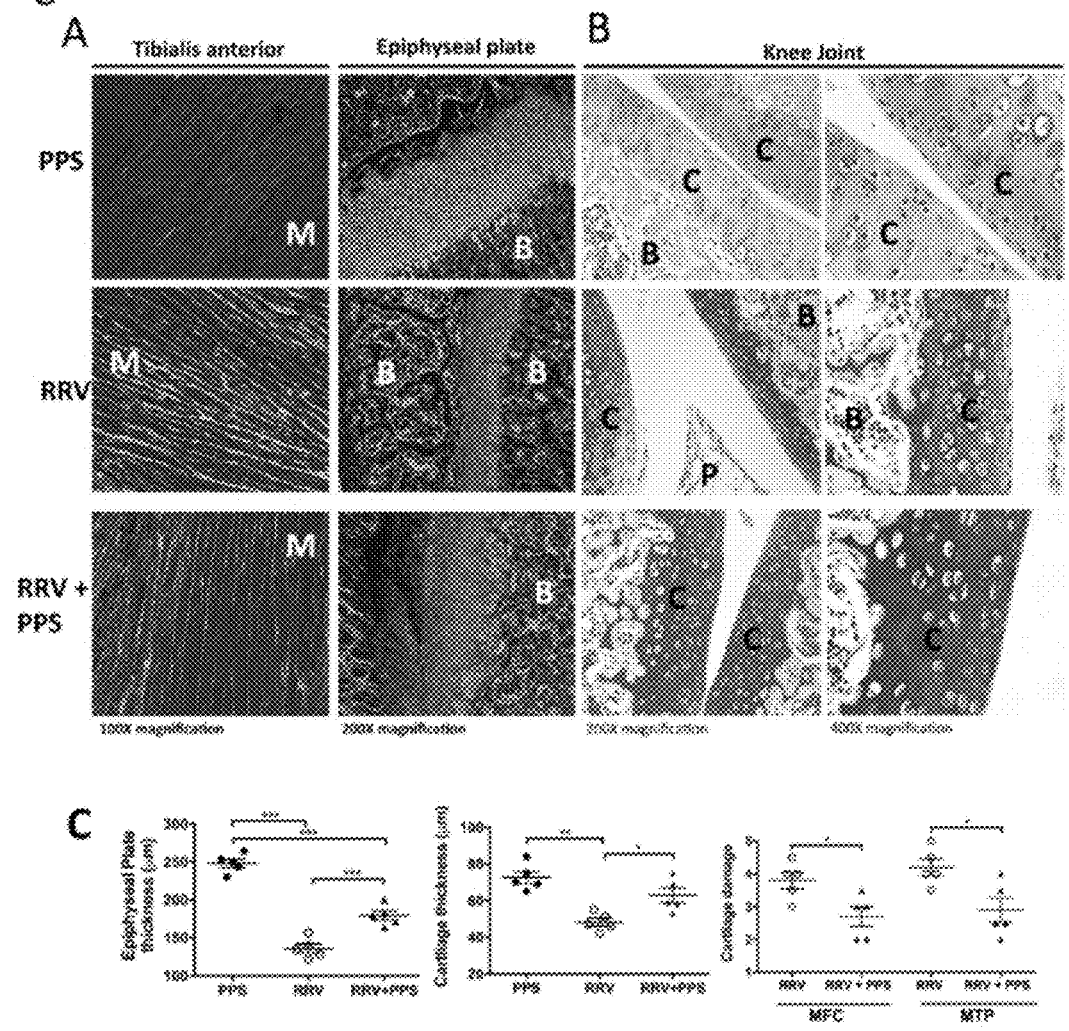

FIG. 5. Pentosan polysulfate treatment protects the joints from RRV-induced cartilage damage.

20-day-old C57BL/6 mice were infected s.c. with $10^4$ pfu RRV or mock-infected with diluent alone then either treated daily i.p. with PPS at 3 mg/kg in 100 μL PBS or mock-treated with PBS alone. For histological analysis, mice were sacrificed at peak disease at 10 days p.i., perfused with 4% PFA, whole legs removed, paraffin-embedded and 5 μm sections generated. Sections were stained with (A) Masson's Trichrome or (B) Safranin O/fast green and showed an increase in collagen fibres, improvement in the skeletal muscle tissue morphology and protection of the proteoglycan matrix with treatment. Annotations; (B) bone, (C) cartilage. (P) pannus, (M) muscle. Images are representative of at least 5-8 mice per group. (C) The width of cartilage and epiphyseal plate from mice were measured in five areas of per mouse and averaged with each point representing one mouse. Cartilage degradation from the medial femoral condyle (MFC) and the medial tibia plateau (MTP) of at least five mice per group was assessed as outlined in the methods with mock control mice showing a score of 1. Data represent mean±SEM of 5 mice per group.

Figure 6:
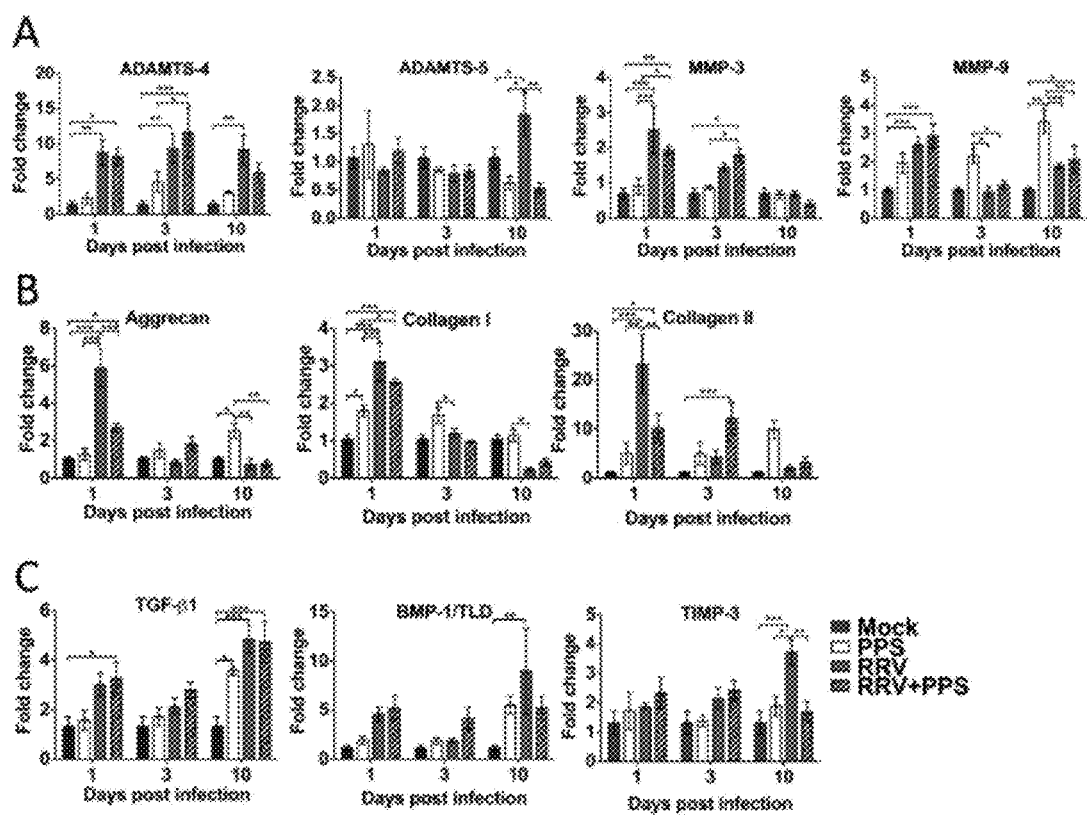

FIG. 6. Pentosan polysulfate treatment counteracts the dysregulation of the cartilage matrix components caused by RRV-infection.

PPS treatment significantly reduced the early expression of aggrecan (SEQ. ID. NO. 2) and collagen II (SEQ. ID. NO. 4) and the expression of ADAMTS-5 (SEQ. ID. NO. 7) and TIMP-3 (SEQ. ID. NO. 10) at peak disease. 20-day-old C57BL/6 mice were infected s.c. with $10^4$ pfu RRV or mock-infected with diluent alone then either treated daily i.p. with PPS at 3 mg/kg in 100 μL PBS or mock-treated with PBS alone (mock-infected mock-treated=Mock control, mock-infected PPS-treated=PPS alone, RRV-infected mock-treated=RRV alone, RRV-infected PPS-treated=RRV+PPS). At days 1, 3 and 10 p.i. joint tissues were removed, RNA extracted and real time PCR performed to evaluate gene regulation of key mediators of the proteoglycan matrix of joint cartilage. Results were normalised to the housekeeping gene HPRT1 and are expressed as fold of change compared to the mock control samples. Each data point represents the mean+/−standard error of 5 to 6 mice and is representative of two independent experiments. *p<0.05, p<0.01, *p<0.001 using two-way ANOVA with Bonferroni post test.

Figure 7:
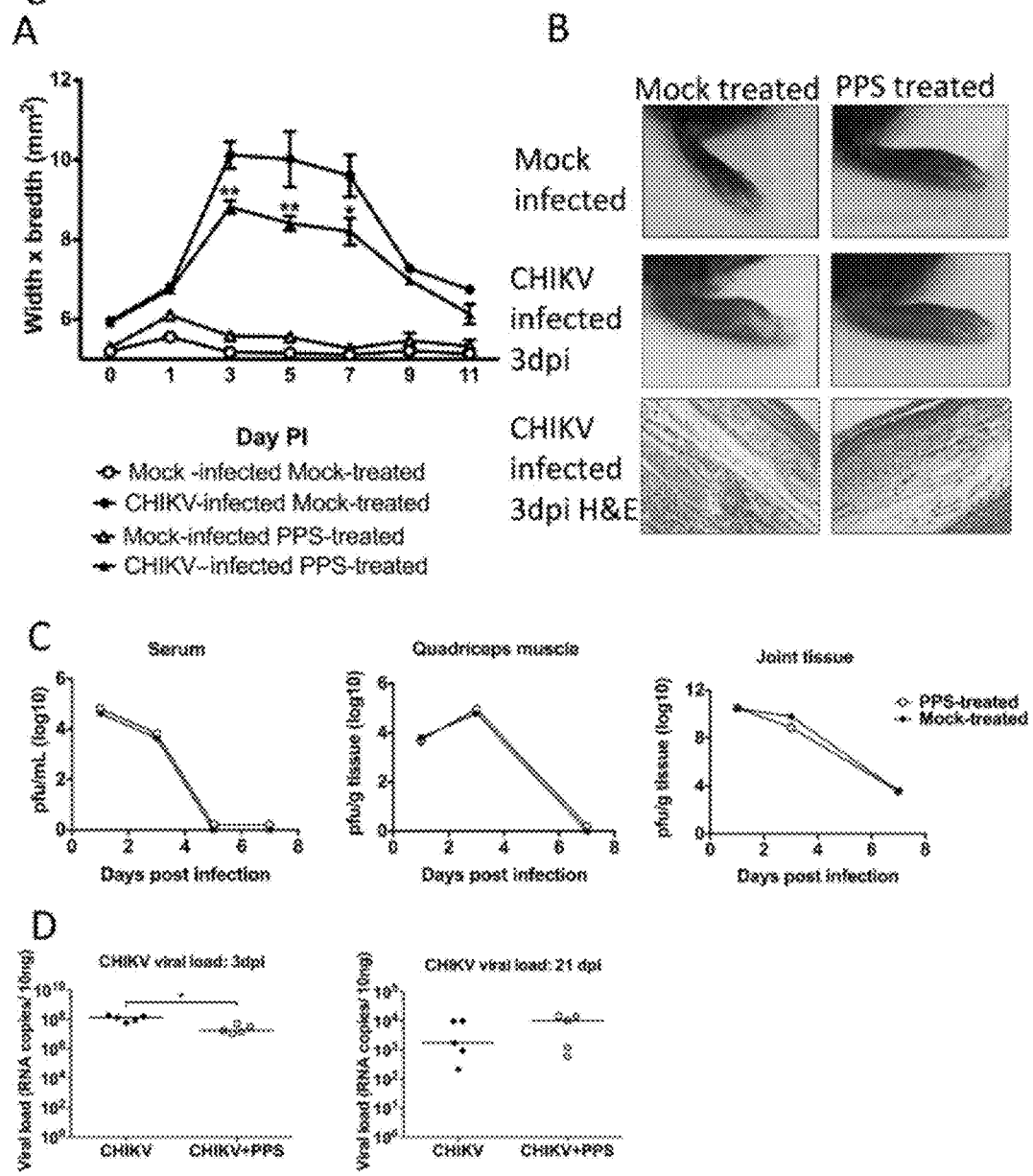

FIG. 7. Pentosan-polysulfate reduces the severity of acute CHIKV-inflammation without affecting the kinetics of viral infection.

25-day-old C57BL/6 mice were infected s.c. with CHIKV or mock-infected with diluent alone then either treated daily i.p. with PPS at 3 mg/kg in 100 μL PBS or mock-treated with PBS alone. (A) CHIKV-induced footpad swelling was assessed daily by measuring the height and width of the perimetatarsal area of the hind foot. PPS treatment resulted in a significant reduction in swelling. (B) H&E stained histological analysis showed PPS treatment decreased the level of inflammatory infiltrates in CHIKV-infected mouse joints at peak swelling 3 days p.i. Both infectious virus and viral RNA levels were measured indicating PPS-treatment did not affect viral clearance. At days 1 and 3 and 7 p.i. the serum, quadriceps and ankle tissues were harvested, homogenised and the viral load determined by (C) plaque assay on Vero cells for infectious virus or (D) by qPCR for viral RNA in joint tissues with CHIKV E2 specific primers. Each data point represents a single mouse, line indicates the median value. **p<0.01 using two-way ANOVA with Bonferroni post test for foot swelling and plaque assay and Mann Whitney for PCR.

FIG. 8. PPS-treatment alters soluble factors in CHIKV-inflammatory disease.

25-day-old C57BL/6 mice were infected with CHIKV or diluent alone then either treated daily i.p. with PPS or mock-treated with PBS alone. (A) Kinetics of IL-10 were altered with PPS-treatment. Grey line indicates the level of mock control. Each data point represents the mean+/− standard error of 5 to 6 mice. *p<0.05, p<0.01, *p<0.001 using two-way ANOVA with Bonferroni post test. Astrices directly on top of bars are compared to mock control levels. (B) Levels pro-inflammatory factors were decreased at peak swelling by day 3 p.i. with PPS treatment *p<0.05, p<0.01, *p<0.001 one-way ANOVA with Tukey's post test.

DESCRIPTION OF EMBODIMENTS

The inflammation arising out of the alphavirus infection is in the joints and/or muscles. Alternatively, the inflammation may be confined to the joints or it may be confined to the muscles. In some embodiments, the inflammation will be in both the joints and the muscles.

Although the present invention is directed towards alphavirus infections generally, in some embodiments, the alphavirus infection will be selected from the group consisting of Ross River virus, chikungunya virus and Barmah Forest virus.

In particular, the present invention in one embodiment is directed towards Ross River virus.

In particular, the present invention in another embodiment is directed towards chikungunya virus.

In particular, the present invention in another embodiment is directed towards Barmah Forest virus.

Administration of the effective amount of pentosan polysulfate to a subject infected with an alphavirus is parenteral.

In some embodiments when a joint is suffering from inflammation, administration is intra-articular.

In other embodiments when a muscle is suffering from inflammation, administration is intra-muscular.

Generally, a daily dose of pentosan polysulfate will be administered. Such dosing may be into one or more joints, one or more muscles, or into both one or more joints and muscles. Alternatively, a single dose may be administered intravenously to treat inflammation in both joints and muscles.

It is, however, within the scope of the invention to administer on two more occasions on a daily basis, depending on the severity of the symptoms of the subject.

Of course it will be recognised that treatment to reduce cartilage damage is undertaken by intra-articular or intravenous administration.

Based on the animal studies disclosed herein, the amount to be administered is within the range of from 0.1 to 5.0 mg/kg body weight of subject.

In some embodiments, the amount to be administered is within the range of from 1.0 to 5.0 mg/kg body weight of subject.

In some embodiments, the amount to be administered is within the range of from 2.0 to 5.0 mg/kg body weight of subject.

Treatment of subjects is by administration to the subject of pentosan polysulfate. Owing to its solubility and ready availability, preferably the sodium salt of pentosan polysulfate is used. However, other salts such as magnesium and calcium may also be used.

Commercially, Bene-PharmaChem has supplied their PPS in 1 ml glass ampoules containing 100 mg PPS/ml. Because of the ready availability of this sterile injectable product it is preferred to be used in the present invention for treating humans.

The Bene-PharmaChem product comprises: sodium pentosan polysulfate (PPS) 100 mg, sodium phosphate 2.2 mg, sodium hydrogen phosphate 6.8 mg, adjusted to pH 6.5 with sodium hydroxide and water for injection, USP, qs. 1 mL.

It is, however, within the scope of this invention to use alternative formulations. For example, standard textbooks in the field of this invention, such as Remington's Practice of Pharmacy teach such alternatives.

Likewise, for veterinary applications, a product such as Cartrophen Vet® (Biopharm Australia) may be used.

In order to better understand the nature of this invention, set out below is a description of a series of experiments carried out to demonstrate the effectiveness of PPS in the treatment of subjects infected with an alphavirus and suffering from joint and/or muscle inflammation and cartilage damage.

Methods

Virus and Cells. Stocks of the wild-type T48 strain of RRV were generated from the full-length T48 cDNA clone (kindly provided by Dr Richard Kuhn, Purdue University) (20). Stocks of CHIKV Mauritius strain were propagated in BHK-21 cells. All titrations were performed by plaque assay on Vero cells as described previously (21).

Mice. C57BL/6 wild type (WT) mice were obtained from the Animal Resources Centre (Perth, Australia) and bred in-house. All animal experiments were performed in accordance with the guidelines set out by the Griffith University Animal Ethics Committee. C57BL/6 mice of twenty- to twenty-five day old, were inoculated subcutaneously (s.c.) with $10^4$ pfu virus. Injections of RRV in PBS to a volume of 50 μL was in the thorax as described previously (11), and CHIKV in PBS to a volume of 20 μL the ventral side of the footpad as described previously (10). Mock-infected mice were inoculated with PBS alone. Mice were weighed and scored for disease signs every 24 h. RRV disease scores were assessed based on animal strength and hind-leg paralysis as outlined previously (22). Swelling of the footpad induced by CHIKV was assessed by measuring the height and width of the perimetatarsal area of the hind foot using Kincrome digital vernier calipers.

Treatment with pentosan polysulfa.te (Cartrophen Vet®, Biopharm Australia) or vehicle alone was given intraperitoneally (i.p.) at 3 mg/kg in 100 μL PBS (vehicle), daily for the duration of the experiment, commencing from the day of virus infection. In long-term experiments, PPS treatment was delivered orally by adding to drinking water at a concentration of 100 mg/L which is equivalent to a dose of 25 mg/kg/day based on the daily water consumption of a C57BL/6 mouse as previously reported (23). Using the human to animal conversion outlined by Regan-Shaw et al., (24) 25 mg/kg/day is the equivalent of the human dose of 2 mg/kg which is the recommended dose for Elmiron®.

Histology. Mice were sacrificed and perfused with 4% paraformaldehyde (PFA). Tissues were collected and fixed in 4% PFA, followed by paraffin embedding. Ankles and knee joints were decalcified prior to embedding. Sagittal sections of five micron thickness were prepared and stained with haematoxylin and eosin (H & E), Masson's trichrome or Safranin O/Fast Green. Cartilage thickness and damage was measured at 200× magnification from the medial femoral condyle (MFC) and the medial tibial plateau (MTP) by averaging five random points of measurement (separated by at least 20 μM of distance) per region per mouse and graphed as the mean±SEM of 5 mice per group. Epiphyseal thickness was measured from central sagittal sections by averaging five random points of measurement (separated by at least 20 μM of distance) per region per mouse and graphed as the mean±SEM of 5 mice per group system. Cartilage degradation from the medial femoral condyle (MFC) and the medial tibial plateau (MTP) was assessed according to a modified semi-quantitative scoring system of Glasson et al., (25) where 1=normal cartilage; 2=alteration of the proteoglycan matrix assessed by Safranin O stain; 3=alteration of the proteoglycan matrix and loss of lamina splendens; 4=a score of 2-3 thinning either the transitional or radial cartilage; 5=a score of 2-3 plus thinning of both the transitional and radial layers.

Multiplex. The level of serum cytokines was determined using multiplex bead arrays kits according to the manufacturer's instructions (Bio-Plea Pro Mouse Cytokine 23-Alex kits) (Biorad, Hercules, Calif.). Data was acquired using a Luminex 200™ (Biorad) and analysed using the Bio-plea Manager™ 6.1 software (Biorad).

Real-Time PCR. Preparation of RNA was performed from cell pellets using TRIzol (LifeTechnologies, Victoria. Australia) according to the manufacturer's instructions. Quantification of total RNA was measured by NanoDrop 1000 spectrophotometer (Thermo Scientific, Victoria, Australia). Extracted total RNA (20 ng/µL) was reverse-transcribed using an oligo (dT) primer and reverse transcriptase (Sigma Aldrich, Sydney, Australia) according to the manufacturer's instructions.

Gene expression-SYBR® Green Real-time PCR was performed using 10 ng of template cDNA on a CFX96 Touch™ Real-Time PCR System in 96-well plates, using QuantiTect Primer Assay kits (Qiagen, Hilden, Germany) for HPRT1, or purchased from primers from Sigma-Aldrich with the sequences outlined in table 1.

Viral load quantification-Standard curve was generated using serial dilutions of RRV T48 infectious plasmid DNA as described previously (26). Quantification of viral load was performed using SsoAdvanced Universal Probes Supermix (BioRad) in 12.5 µL reaction volume to detect nsP3 region RNA (table 1) (26).

All reactions were performed using BioRad CFX96 Touch™ Real-Time PCR Detection System on 96-well plates. Cycler conditions were as follows: (i) PCR initial activation step: 95° C. for 15 min, 1 cycle and (ii) 3-step cycling: 94° C. for 15 sec, follow by 55° C. for 30 sec and 72° C. for 30 sec. 40 cycles. Dissociation curve was acquired using CFX Manager™ software to determine specificity of amplified products. Standard curve was plotted and copy numbers of amplified products were interpolated from standard curve using Prism Graphpad software to determine viral load. The fold change in mRNA expression relative to mock-infected samples for each gene was calculated with the ΔΔCt method. Briefly, ΔΔCt=ΔCt (RRV-infected)−ΔCt (Mock-infected) with ΔCt=Ct (gene of interest)−Ct (housekeeping gene-HPRT). The fold change for each gene was calculated as $2^{-\Delta\Delta Ct}$.

Detection of leukocyte infiltrates in quadriceps. Quadriceps muscles were removed and processed as described previously (10). Briefly, tissues were incubated with 3 mg/Ml collagenase IV and 1 mg/mL DNase I in 100 µL RPMI 1640 at 37° C. for 1.5 h then resuspended in 5 mL RPMI and passed through a 40 µm cell strainer. Cells were washed, pelleted and treated with 1× RBC lysis buffer for 5 min, and counted. To determine percentages and numbers of

TABLE 1

Primer sequences

| Gene | Forward | Reverse | SEQ. ID.* |
|---|---|---|---|
| TGFβ | CAA CGC CAT CTA TGA GAA AAC C | AAG CCC TGT ATT CCG TCT CC | 1 |
| Aggrecan | GCC CAA GAA CAG TAC GGT | AAT TGC TAG GTT GGT TGA CCC A | 2 |
| Collagen I | CAG AAC ATC ACC TAC CAC TGC AA | TTC AAC ATC GTT GGA ACC CTG | 3 |
| Collagen II | AGA ACA GCA TCG CCT ACC TG | CTT GCC CCA CTT ACC AGT GT | 4 |
| BMP-1/mTLD | AGC AGG CTG CAG TTC GAC AGC | TCA GAA TGT GTT CCG GGC ATA GTG CAT | 5 |
| ADAMTS-4 | CAC TCA CTT CCT GGA CAA GGA TGG TTA T | AAA GTC GTC GGT AGA TGG A | 6 |
| ADAMTS-5 | GAT GAT CAC GAA GAG CAC TAC GA | TCA CAT GAA TGA TGC CCA CAT | 7 |
| MMP-3 | TGG AGC TGA TGC ATA AGC CC | TGA AGC CAC CAA CAT CAG GA | 8 |
| MMP-9 | GGA ACT CAC ACG ACA TCT TCC A | GAA ACT CAC ACG CCA GAA GAA TTT | 9 |
| TIMP-3 | GGC ACT CTG GTC TAC ACT TTT ATT AAG CA | CAG AGG CTT CCG TGT GA | 10 |
| RRV nsp3 primer | CCG TGG CGG GTA TTA AT | TCA AAC ACT CCC GTC GAC AAC AGA | 11 |
| RRV nsp3 Probe | ATT AAG AGT GTA GCC ATC-C | | 12 |

*A sequence ID listing is attached hereto as Appendix A.

specific leukocyte populations, cells were treated with Fc Block (2.4G2; BD) for 5 min at 4° C. and labelled with fluorochrome-conjugated anti-mouse antibodies, including anti-CD3-FITC (145-2C11, BD), anti-CD19-APC (MB19-1, eBioscience), anti-CD11b-PE (M1/70, BD), anti-Gr1-APC (RB6-8C5, eBioscience) and anti-pan-NK/NKT antigen-PE (U5A2-13, BD) in various combinations in the presence of biotinylated anti-CD45 (30-F11, eBioscience), followed by treatment with streptavidin PE-Cy7 at 4° C. for 30 min. Cells were resuspended in 500 µL PBS containing 2% FCS and 1 µg/mL propidium iodine (PI), and analysed by the CyAn ADP flow cytometer (Beckman Coutler) with Kaluza software.

Statistical analysis. Body mass, plaque assay, multiplex (FIGS. 4C and 8A), real-time PCR (FIG. 6) and joint swelling were analysed using two-way ANOVA with Bonferroni post-test. Real-time PCR (FIG. 1D), multiplex (FIGS. 4B and 8B) and histology (FIG. 5C) were analysed using a one-way ANOVA with a Dunnett's or Tukey's post-test. Flow cytometry data and histology (FIG. 1C) were analysed using unpaired Students t-test. All data was tested for normality using the D'Agostino-Pearson normality test prior to analysis with these parametric tests. Clinical scores and and real-time PCR for viral load were analysed using the non-parametric Mann-Whitney test. Statistics were performed with GraphPad Prism 5.0

Results

Ross River virus infection stimulates the production of proteases ADAMTS-4 (SEQ. ID. NO. 6), MMP-3 (SEQ. ID. NO. 8), and MMP-9 (SEQ. ID. NO. 9) and causes damage to the articular cartilage in joints.

To determine if RRV infection affects the cartilage of joints, we infected C57BL/6 mice with RRV and isolated joint tissue for histological analysis. At peak disease, extensive joint inflammation was observed along with pannus-like formation and thinning of the articular cartilage in H&E stained sections (FIG. 1A). Further analysis of joint sections, stained with Safranin O, revealed considerable disruption of the proteoglycans in the cartilage matrix, as seen by the difference in Safranin O staining intensity (which is directly proportional to the proteoglycan content) between infected and mock tissues (FIG. 1B) (27). Quantification of cartilage thickness and damage was measured from the MFC and MTP and showed RRV-infection results in an average 20 µm reduction in articular cartilage thickness and cartilage damage characterised by alteration of the proteoglycan matrix and loss of lamina splendens (FIG. 1C). Furthermore, RRV-infection resulted in an early significant increase (24 hours p.i.) of the enzymes; A disintegrin and metalloproteinase with thrombospondin motifs (ADAMTS)-4 (SEQ. ID. NO. 6) ($p<0.001$), matrix metalloproteinase (MMP)-3 (SEQ. ID. NO. 8) ($p<0.05$) and MMP-9 (SEQ. ID. NO. 9)($p<0.01$) compared to mock infected controls. These are known to cause cartilage damage by degrading aggrecan (SEQ. ID. NO. 2), collagen, proteogylcans and the extracellular matrix (FIG. 1Di). At peak disease, stimulators of cartilage growth, matrix-transforming growth factor (TGF) β1 ($p<0.01$) and bone morphogenetic protein (BMP)-1 ($p<0.001$) were also significantly increased in response to RRV-infection compared to mock-infected controls (FIG. 1Dii). The results suggest that RRV infection results in cartilage degradation and thinning which is associated with arthritic disease symptoms.

Pentosan polysulfate reduces the severity of RRV-induced disease and inflammation To assess the potential of PPS as a treatment strategy in alphaviral disease, mice were infected with RRV or mock-infected with PBS alone and then treated i.p. with either PPS at 3 mg/kg or with vehicle daily. PPS treatment resulted in a 65% decrease ($p>0.05$) in clinical disease score in RRV-infected mice (FIG. 2A) and a corresponding protection from disease-associated weight loss ($p>0.001$) (FIG. 2B).

To better characterise the reduction in disease, we assessed inflammation and tissue damage in RRV-infected mock and PPS-treated mice. Tissues from RRV-infected mice were collected at the start and end of peak disease (day 7 and 10 p.i.) for histological analysis and flow cytometry. No inflammation was observed in the quadriceps muscle or ankle joint of control mock-infected mock-treated or mock-infected PPS-treated mice (FIG. 2C). Consistent with previous studies, RRV-infected mock-treated mice showed extensive inflammation and myositis in quadriceps muscle at day 7 p.i. (FIG. 2C,D) and around the ankle joint (FIG. 2C) (11, 21, 22, 28). In contrast, RRV-infected PPS-treated mice showed markedly reduced numbers of infiltrating cells in both the muscle and the joint tissues (FIG. 2C).

In order to characterise the effect of PPS treatment on both lymphoid and myeloid infiltrating cells, we analysed the cell populations in the quadriceps muscles at days 7 and 10 p.i. by flow cytometry. At day 7 p.i. PPS treatment uniformly reduced the numbers of all $CD45^+$ infiltrating leukocytes including reductions ($p<0.05$) in the monocytes, T cell and NK cell populations (FIG. 2D). By day 10 p.i. PPS treatment showed a decrease in the T cell and NK cell populations ($p<0.05$) with similar numbers of $CD45^+$ cells and monocytes (FIG. 2D). At day 10 p.i. treatment also altered the NK cell to total cell ratio resulting in a reduction in the overall percentage of NK cells in the quadriceps muscle (data not shown).

Reduced disease in treated mice is not due to decreased viral burden.

Viral titres in the serum of PPS-treated and mock-treated mice were comparable at all days tested, indicative of equivalent systemic replication (FIG. 3A). Similarly, RRV titres recovered from quadriceps muscles were comparable (FIG. 3A). Interestingly, RRV titres in the ankle tissues showed the most variation between PPS-treated and mock-treated mice (FIG. 3A). By day 3 p.i. there was a slight reduction in RRV titres for PPS-treated mice; by day 7 p.i titres were comparable; and then by day 10 p.i. RRV titres in PPS-treated mice were elevated compared to mock-treated mice ($p<0.05$). The results from day 10 p.i. suggest that PPS-treatment may have an effect on viral clearance within the joint. To assess viral clearance, qPCR to quantify viral RNA was performed on the joint tissues (FIG. 3B). Although the trend appears to suggest a lower level of specific RRV RNA in the joint tissue of PPS-treated RRV-infected mice in the joint at ay 10 p.i., this was not statistically significant compared to mock-treated mice, confirming that PPS-treatment does not affect viral clearance.

Treatment with pentosan polysulfate increases the level of anti-inflammatory IL-10 and decreases pro-inflammatory factors associated with RRV disease.

A range of pro-inflammatory factors and chemoattractants mediate or contribute to alphaviral disease (29). To elucidate whether PPS-treatment affects the production of soluble immune mediators during RRV infection, sera from PPS-treated and mock-treated mice were analysed using multiplex and compared to mock-infected, PPS-treated or mock-treated mice. As expected, RRV infection resulted in an increase ($p<0.05$) of pro-inflammatory factors (both cytokines and chemoattractants) at peak disease (FIG. 4). PPS-treatment also altered the levels of the M2 anti-inflammatory cytokine IL-10. IL-10 kinetics corresponded to the kinetics of disease with serum levels increasing over time in RRV-infected, mock-treated mice. PPS-treatment resulted in an early surge of IL-10 in RRV-infected mice, being significantly elevated at both days 1 and 3 p.i. ($p<0.001$ and 0.01 respectively) (FIG. 4A). Additionally, PPS treatment significantly reduced the serum levels of IL-1α, IL-2, IL-6, CCL-2 and MIP-1α at peak disease ($p<0.05$) (FIG. 4B).

Pentosan polysulfate treatment protects the joints from cartilage damage associated with RRV infection.

Recently we showed that RRV could infect osteoblasts and infection results in systemic bone loss including the tibial epiphysis and vertebrae (30-32). To determine the effect of PPS treatment on RRV-induced muscle and joint damage, the tissues of RRV-infected and mock-infected PPS-treated and mock-treated mice were processed for histological analysis using Masson's trichrome and Safranin O/Fast Green staining. Masson's trichrome staining of the tibialis anterior showed PPS treatment protected the morphology of striations within the skeletal muscle with sections of collagen formation characteristic of muscle repair and fibrosis (33). PPS treatment also prevented RRV-induced thinning of the epiphyseal plate, protecting against cartilage loss (FIG. 5A, C). Safranin O/Fast Green staining of the cartilage in the knee joint revealed that PPS treatment protected the proteoglycan matrix of the articular cartilage, preventing the loss of articular cartilage observed in RRV-infected mock-treated mice as well as maintaining chondrocyte morphology (FIG. 5B, C).

To further characterise the mechanism of PPS treatment we analysed the genes involved in enzyme degradation of cartilage (ADAMTS-4 (SEQ. ID. NO. 6), ADAMTS-5 (SEQ. ID. NO. 7), MMP-3 (SEQ. ID. NO. 8), and MMP-9 (SEQ. ID. NO. 9)), stimulation of cartilage protection and synthesis (TGF-β1 and BMP-1) and cartilage matrix proteins (aggrecan (SEQ. ID. NO. 2), collagen I (SEQ. NO. ID. 3), and collagen II (SEQ. ID. NO. 4)). As shown in FIG. 1D, RRV-infection caused an increase in ADAMTS-4 (SEQ. ID. NO. 6), which remains elevated at day 3 p.i ($p<0.01$), but drops by the time of peak disease (day 10 p.i), where there was a surge in ADMATS-5 (SEQ. ID. NO. 7). RRV-infection also resulted in a late rise (at peak disease) of tissue inhibitor of metalloproteinases (TIMP)-3 ($p<0.001$); known to inhibit both ADAMTS-4 (SEQ. ID. NO. 6) and ADAMTS-5 (SEQ. ID. NO. 7) (FIG. 6A, 6C). PPS-treatment significantly reduced the levels of ADAMTS-5 (SEQ. ID. NO. 7) and TIMP-3 (SEQ. ID. NO. 10) at peak disease ($p<0.01$), but not at the early stages of infection. RRV-infection also resulted in an increase of cartilage components aggrecan (SEQ. ID. NO. 2), collagen I (SEQ. ID. NO. 3), and collagen II (SEQ. ID. NO. 4), that is largely reduced with PPS-treatment (FIG. 6B). The genes associated with signalling pathways for cartilage development (TGF-β1 and BMP-1) and the metalloproteinases were unaffected by PPS (FIG. 6).

Pentosan polysulfate treatment is a safe long-term treatment strategy for chronic RRV disease.

To assess PPS-treatment for a long-term treatment in patients with chronic symptoms, mice were RRV-infected and treated orally with PPS or mock-treated in drinking water. Long-term PPS treatment resulted in no adverse clinical signs in the mice for the 3-month duration of the experiment. RRV-infected mock-treated mice showed extended disruption of the cartilage components with a three-fold elevation of aggrecan (SEQ. ID. NO. 2) ($p<0.01$) (Table 2). PPS-treated mice showed less joint damage and significantly decreased the expression of aggrecan (SEQ. ID. NO. 2) back to base-line levels ($p<0.001$). The levels of ADAMTS-4 (SEQ. ID. NO. 6) expression were also reduced ($p<0.01$).

TABLE 2

Long-term PPS treatment decreases the expression of aggrecan (SEQ. ID. NO. 2) and ADAMTS-4 (SEQ. ID. NO. 6) in RRV infection.

| | Mock | | | RRV | | | RRV + PPS | | |
|---|---|---|---|---|---|---|---|---|---|
| Gene | Fold Change | SEM | n | Fold Change | SEM | n | Fold Change | SEM | n |
| ADAMTS-4 | 0.8345 | 0.2037 | 6 | 1.2261 | 0.2377 | 5 | 0.1689** | 0.2998 | 5 |
| ADAMTS-5 | 1.0854 | 0.3209 | 6 | 1.5759 | 0.3730 | 5 | 0.8305 | 0.1796 | 5 |
| MMP-3 | 1.1335 | 0.3492 | 6 | 1.6958 | 0.4408 | 5 | 2.5028 | 1.2218 | 5 |
| MMP-9 | 1.0066 | 0.0833 | 6 | 1.0858 | 0.2012 | 5 | 0.8604 | 0.2477 | 5 |
| Aggrecan | 1.0235 | 0.1579 | 3 | 2.9417 | 0.2865 | 4 | 0.6105*** | 0.1050 | 5 |
| Collagen I | 1.0128 | 0.1178 | 3 | 0.8550 | 0.1417 | 5 | 0.4014 | 0.0748 | 5 |
| Collagen II | 1.0357 | 0.1793 | 3 | 0.9584 | 0.2358 | 5 | 0.1719 | 0.0556 | 5 |
| TGF-β1 | 1.0243 | 0.1525 | 3 | 1.5343 | 0.2852 | 5 | 0.4010 | 0.0587 | 5 |
| BMP-1 | 1.0597 | 0.2678 | 3 | 1.6204 | 0.2950 | 5 | 1.4697 | 0.7026 | 5 |
| TIMP-3 | 1.3321 | 0.7729 | 6 | 1.4287 | 0.3184 | 5 | 0.6328 | 0.1368 | 5 |

Pentosan polysulfate is a potential treatment for CHIKV-induced inflammation, reducing disease by altering the cytokine response.

Given the expanding range of the alphavirus-CHIKV, together with the current lack of therapeutic treatment options, we sought to determine the broader application of PPS on alleviating CHIKV-induced disease. PPS treatment decreased the level of joint swelling of CHIKV-infected mice corresponding to a reduction in inflammatory cells infiltrating into the joint (FIG. 7A, B). Furthermore, as seen in RRV-infection, PPS-treatment did not affect the kinetics of virus infection (FIG. 7C) and did not increase the viral persistence in the joint tissues, with similar levels of viral RNA detected three weeks p.i. (FIG. 7D). The reduced disease also correlated to an early surge in anti-inflammatory IL-10 (FIG. 8A) and reduced the levels of soluble factors CCL-2, IL-6, IL-9 and G-CSF at peak disease (day 3 p.i.) (FIG. 8B). These collective results, whereby PPS reduces the disease severity of two critical alphaviral diseases suggest that PPS may be a promising broad-range treatment for alphavirus disease manifestations in general.

Discussion

The mechanisms by which alphaviruses trigger arthritis and myositis are the focus of ongoing studies. Alphavirus-induced disease has many similarities to rheumatoid arthritis (RA) including common inflammatory pathways and the key involvement of macrophages (11,12). The innate immune response is critical in the pathogenesis of alphaviral disease, mediating cell recruitment, viral clearance and inflammation (28, 29, 34). In particular, monocytes and macrophages are the major cellular contributors to disease progression and severity (29). In RA, monocytes play a significant role in disease development and cartilage destruction through the production of pro-inflammatory factors. (35). Despite these clear similarities, the potential of alphavirus infection to damage the articular cartilage in the joint tissues has not been investigated. We now propose that, analogous to RA, RRV-infection leads to an immune poly-arthritis that causes cartilage thinning that contributes to clinical signs associated with alphaviral disease.

It has long been recognised that the joint tissue is a critical site of viral replication, and we recently identified osteoblasts as a source of infectious virus, being susceptible to RRV infection (31). We showed that RRV-infection results in bone loss by disrupting the receptor activator of nuclear factor κβ ligand (RANKL) and osteoprotegerin (OPG) ratio (31). We now describe thinning of articular cartilage in an RRV disease mouse model correlating to a significant increase in metalloproteinases including ADAMTS-4 (SEQ. ID. NO. 6) and ADAMTS-5 (SEQ. ID. NO. 7). These result in histopathological findings similar to mild onset RA.

A recent study, using $CCR2^{-/-}$ mice infected with CHIKV, showed that when normal monocyte trafficking is disrupted by this receptor knockout the major inflammatory infiltrates became neutrophil dominant (36). This replaces the usual macrophage dominance of the cellular response observed in alphavirus infections. Comparing the histopathological findings in the feet of CHIKV-infected wild-type (WT) and $CCR2^{-/-}$ mice, Poo et al (36) observed that the neutrophil shift resulted in cartilage damage. We also observe cartilage thinning in immunocompetent C57BL/6 mice (with functional macrophage trafficking) following RRV infection, demonstrating that macrophages may also play a critical role in RRV-induced inflammation including cartilage thinning.

The use of glycans as novel therapeutics has developed momentum in recent years (37). The interaction of glycans with growth factors, extracellular proteases, protease inhibitors, cytokines/chemokines and adhesive proteins regulate various physiopathologies and diseases including cancer, atherosclerosis and thrombosis (38). In addition many pathogens, including viruses, exploit host glycans to cause infection. The therapeutic potential of this class of molecule to alleviate viral-induced arthritis and inflammatory disease has not been studied and currently remains unknown.

Pentosan polysulfate is a semisynthetic polysaccharide derivative that chemically and structurally resembles other GAGs, including heparin. In contrast to many other GAGs, PPS is bioavailable in both its injectable and oral forms and produces limited toxic side effects, even when administered in high doses (39). In a clinical setting, PPS has been used as an anti-thrombotic agent for several decades, due to its ability to bind preferentially to the glycocalyx of circulating blood cells (40). In more recent times, PPS has been identified as having anti-inflammatory properties and is currently approved in the United States for the management of patients with interstitial cystitis, having an excellent long-term safety profile (15). Furthermore, injectable forms of PPS are currently used to treat osteoarthritis in veterinary medicine (19).

Given the promising results of PPS treatment of a range of inflammatory conditions particularly arthritis, and the lack of studies on PPS in treating virus-associated pathologies, we tested the efficacy of PPS to treat alphavirus-induced arthritis. PPS treatment significantly reduced the acute disease signs and the muscle and joint inflammation of both RRV- and CHIKV-induced disease. This corresponded to a reduction in serum levels of pro-inflammatory factors at peak disease. In diabetic kidney nephropathy, disease pathogenesis is dependent on the cellular infiltration of macrophages and pro-inflammatory and chemoattractant factors, similar to those associated with alphavirus-arthritis. These include CCL-2, RANTES and CXCL1, TNF-α (29, 41). Our data are consistent with the treatment observed in diabetic nephropathy, in which PPS reduced the macrophage infiltration and suppressed the induction of pro-inflammatory factors (41).

At the onset of RRV-disease (day 6-7 p.i), there is a surge in the levels of IL-10 (42). Of interest to the present study is the recent observation demonstrating that a surge in IL-10 resulted in a phenotype switch of monocytes/macrophages (43, 44). This suggests that IL-10 is part of a repair signal that activates specific cellular and molecular cascades to facilitate tissue recovery (43). PPS-treatment altered the kinetics of RRV-induced soluble pro- and anti-inflammatory factors, promoting a swing to anti-inflammatory cytokines with an early induction of IL-10 that enhances myogenesis (43). Furthermore IL-10 inhibits the synthesis of pro-inflammatory soluble factors including, IL-1α, IL-2, IL-6, TNF-α and CCL-2 (45), previously associated with increased severity of alphaviral disease. Overall the early PPS-induced increase of IL-10 may act to reduce inflammation, but also enhance tissue repair, thereby providing a key mechanism by which PPS-treatment reduces the severity of alphaviral disease.

In addition to the reported action of PPS in reducing pro-inflammatory factors, PPS inhibits both the alternative and classical pathways of complement activation (46). For example, in RRV-pathogenesis, complement activation is essential for the development of severe RRV disease (34). Furthermore, this is specific to RRV-activation of complement via the MBL pathway and is independent of the classical and alternative pathways (28), and therefore it is unlikely that the reduction in RRV disease observed with PPS treatment is due to its effect on complement.

Treatment with PPS also resulted in protection of the i) epiphysis, 2) articular cartilage and 3) proteoglycan matrix. The anti-inflammatory effect of PPS is due in part to its ability to inhibit IL-6 (47). In our results, serum levels of IL-6 were significantly reduced in PPS treated RRV-infected mice at peak disease. We have shown that the disruption of the RANKL and OPG ratio during RRV-infection occurs in an IL-6 dependent manner such that inhibition of IL-6 protects from RRV-induced bone loss (31). Additionally, studies on CCL-2 have recently demonstrated that inhibition of CCL-2 can both inhibit osteoclast differentiation and protect against CHIKV induced bone loss (30, 48). Therefore, it is likely that PPS protection against RRV-induced bone loss is due to its ability to inhibit both IL-6 and CCL-2. PPS also stimulates hyaluronan synthesis by synovial fibroblasts and proteoglycan synthesis by chondrocytes (49). This may explain the observed protection of both the articular cartilage and the proteoglycan matrix in PPS-treated RRV-infected mice. PPS also promotes the proliferation and chondrogenic differentiation of adult human bone marrow mesenchymal stem cells (50), further explaining the PPS protection of articular cartilage thinning that we see in RRV-infection.

Although the molecular mechanism of PPS action remains unclear, PPS can repress MMP, including ADAMTS expression and inflammation, as well as NF-κB activation. It also enhances proteoglycan synthesis, including the production of aggrecan (SEQ. ID. NO. 2) and hyaluronan (49) and has been shown to be efficacious as both a treatment and a prophylactic (51). The results of this study demonstrate that RRV-infection results in cartilage thinning, increasing the levels of ADAMTS-4 (SEQ. ID. NO. 6) and ADMATS-5 (SEQ. ID. NO. 7) (aggrecanase 1 and 2 respectively), which in turn disrupts the proteoglycan matrix in the cartilage, similar to that reported in osteoarthritis. It also has been demonstrated recently that PPS blocks aggrecan (SEQ. ID. NO. 2) breakdown by both binding directly to ADAMTS molecules and inhibiting their action, and by increasing the affinity between ADAMTS and its inhibitor TIMP-3 (SEQ. ID. NO. 10)(52). We therefore hypothesise that one of the underlying mechanisms by which PPS treatment prevents cartilage thinning in RRV-induced arthritis, occurs by blocking aggrecan (SEQ. ID. NO. 2) breakdown.

In humans, long-term clinical use of PPS is extremely well tolerated and highly efficacious for periods greater than 12 months (53). Alphaviruses can produce chronic musculoskeletal ailments over a prolonged period of time. A long-term therapeutic strategy is therefore required for effective treatment of alphavirus-induced arthritis. We have shown that PPS not only alleviates the acute signs of RRV-induced arthritis but also protects the cartilage over the long-term without compromising host viral clearance. Given that PPS promotes an anti-inflammatory immune state without promoting viral persistence, it is an attractive drug-repurposing candidate for the long-term treatment of RRV-associated inflammation and disease.

To date, non-steroidal anti-inflammatory drugs are the primary therapeutic means to alleviate the symptoms of alphavirus-associated inflammatory disease. These drugs can cause a variety of undesired side effects and may compromise immunity in treated patients (54). Studies by our group in the past have examined a number of drug candidates for the treatment of alphavirus disease. Bindarit (a CCL-2 inhibitor), while effective in reducing alphavirus induced arthritis and myositis, is currently not a drug that is available for human use (30, 55). Enbrel, while available for human use, was found to suppress the antiviral response and enhance viral replication thereby worsen disease (56). Similarly, methotrexate, a licensed drug for the treatment of RA, increased the onset of RRV-induced musculoskeletal disease and the influx of inflammatory cell infiltrates into the skeletal muscle tissue (57). Here we show PPS treatment significantly reduced both the acute clinical signs and the inflammation in the muscle (myositis) and the joint (arthritis) in alphavirus disease. Additionally PPS has positive and extensive long-term human safety data, and is available as an approved drug by a number of regulatory authorities globally. We therefore conclude that PPS is a promising therapeutic candidate for alphaviral disease; and may also be effective in other infectious inflammatory conditions.

To this end, the Australian Therapeutic Goods Administration has provided its approval for the evaluation of PPS in four Ross River virus infected subjects. Those subjects were treated with PPS intramuscularly in accordance with the dosage regimen as described herein.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

REFERENCES

1. Burt F J, Rolph M S, Rulli N E, Mahalingam S, Heise M T. 2012. Chikungunya: a re-emerging virus. Lancet 379: 662-671.
2. Noel H, Rizzo C. 2014. Spread of chikungunya from the Caribbean to mainland Central and South America: a greater risk of spillover in Europe? Euro surveillance: bulletin Europeen sur les maladies transmissibles=European communicable disease bulletin 19 (28).
3. Centers for Disease Control (CDC). 2014. First Chikungunya case acquired in the United States reported in Florida. [cited 2014 27th September]; Available from: http://www.cdc.gov/media/releases/2014/p0717-chikungunya.html
4. Pan American Health Organization (PAHO). 2016. Chikungunya. [cited 2016 23rd May]; Available from: http://www.paho.org/hq/index.php?option=com topics& view=article&id=343& Itemid=40931
5. Herrero L, Nelson M, Bettadapura J, Gahan M E, Mahalingam S. 2011. Applications of animal models of infectious arthritis in drug discovery: a focus on alphaviral disease. Curr Drug Targets 12:1024-1036.
6. Manimunda S P, Viiavachari P, Unnoor R. Sugunan A P, Singh S S, Rai S K, Sudeep A B, Muruganandam N, Chaitanya I K, Guruprasad D R. 2010. Clinical progression of chikungunva fever during acute and chronic arthritic stages and the changes in joint morphology as revealed by imaging. Trans R Soc Trop Med Hyg 104: 392-399.
7. Fraser J R, Cunningham A L, Clarris B J, Aaskov J G, Leach R. 1981. Cytology of synovial effusions in epidemic polyarthritis. Aust N Z J Med 11:168-173.
8. Fraser J R, Ratnamohan V M, Dowling J P, Becker G J, Varigos G A. 1983. The exanthem of Ross River virus infection: histology, location of virus antigen and nature of inflammatory infiltrate. J Clin Pathol 36:1256-1263.
9. Soden M, Vasudevan H, Roberts B, Coelen R, Hamlin G, Vasudevan S, La Brooy J. 2000. Detection of viral ribonucleic acid and histologic analysis of inflamed synovium in Ross River virus infection. Arthritis Rheum 43:365-369.
10. Herrero L, Sheng K-C, Jian P, Herr Z, Herring B, Chow A, Chow Y, Hickey M, Morand E, Ng L, Bucala R, Mahalingam S. 2013. MIF receptor CD74 mediates alphavirus-induced arthritis and myositis murine models of alphavirus infection. Arthritis and Rheumatism 65:2724-2736,
11. Herrero L J, Nelson M, Srikiatkhachorn A, Gu R, Anantapreecha S, Fingerle-Rowson G, Bucala R, Morand E, Santos L L, Mahalingam S. 2011. Critical role for macrophage migration inhibitory factor (MIF) in Ross River virus-induced arthritis and myositis. Proc Natl Acad Sci USA 108:12048-12053.
12. Nakaya H I, Gardner J, Poo Y S, Major L, Pulendran B, Suhrbier A. 2012. Gene profiling of Chikungunya virus arthritis in a mouse model reveals significant overlap with rheumatoid arthritis. Arthritis Rheum 64:35:53-3563.
13. Bresnihan B. 1999. Pathogenesis of joint damage in rheumatoid arthritis. J Rheumatol 26:717-719.
14. Otero M, Goldring M B. 2007. Cells of the synovium in rheumatoid arthritis. Chondrocytes. Arthritis Res Ther 9:220.

15. Parsons C L, Mulholland S G. 1987. Successful therapy of interstitial cystitis with pentosanpolysulfate. J Urol 138:513-516.
16. Kumagai K, Shirabe S, Miyata N, Murata M, Yamauchi A, Kataoka Y, Niwa M. 2010. Sodium pentosan polysulfate resulted in cartilage improvement in knee osteoarthritis—an open clinical trial. BMC Clin Pharmacal 10:7.
17. Ghosh P, Edelman J, March L, Smith M. 2005. Effects of pentosan polysulfate in osteoarthritis of the knee: A randomized, double-blind, placebo-controlled pilot study. Curr Ther Res Clin Exp 66:552-571.
18. Ghosh P. 1999. The pathobiology of osteoarthritis and the rationale for the use of pentosan polysulfate for its treatment. Setnin Arthritis Rheum 28:211-267.
19. Kongtawelert P, Brooks P M, Ghosh P. 1989. Pentosan polysulfate (Cartrophen) prevents the hydrocortisone induced loss of hyaluronic acid and proteoglycans from cartilage of rabbit joints as well as normalizes the keratin sulfate levels in their serum. J Rheumatol 16:1454-1459.
20. Kuhn R J, Niesters H G, Hong Z, Strauss J H. 1991. Infectious RNA transcripts from Ross River virus cDNA clones and the construction and characterization of defined chimeras with Sindbis virus. Virology 182:430-441.
21. Lidbury B A, Simeonovic C, Maxwell G E, Marshall I D, Hapel A J. 2000. Macrophage-induced muscle pathology results in morbidity and mortality for Ross River virus-infected mice. J Infect Dis 181:27-34.
22. Morrison T E, Whitmore A C, Shabman R S, Lidbury B A, Mahalingam S, Heise M T. 2006, Characterization of Ross River virus tropism and virus-induced inflammation in a mouse model of viral arthritis and myositis. J Virol 80:737-749.
23. Bachmanov A A, Reed D R, Beauchamp G K, Tordoff M G. 2002. Food intake, water intake, and drinking spout side preference of 28 mouse strains. Behavior genetics 32:435-443.
24. Reagan-Shaw S, Nihal M, Ahmad N. 2008. Dose translation from animal to human studies revisited. FASEB J 22:659-661.
25. Glasson S S, Chambers M G, Van Den Berg W B, Little C B. 2010. The OARSI histopathology initiative—recommendations for histological assessments of osteoarthritis in the mouse. Osteoarthritis Cartilage 18 Suppl 3:S17-23.
26. Shabman R S, Rogers K M, Heise M T. 2008, Ross River virus envelope glycans contribute to type I interferon production in myeloid dendritic cells. J Virol 82:12374-12383.
27. Camplejohn K L, Allard S A. 1988. Limitations of safranin 'O' staining in proteoglycan-depleted cartilage demonstrated with monoclonal antibodies. Histochemistry 89:185-189.
28. Gunn B M, Morrison T E, Whitmore A C, Blevins L K, Hueston L, Fraser R J, Herrero L J, Ramirez R, Smith P N, Mahalingam S, Heise M T. 2012. Mannose binding lectin is required for alphavirus-induced arthritis/myositis. PLoS Pathog 8:e1002586.
29. Lidbury B A, Rulli N E, Suhrbier A, Smith P N, McColl S R, Cunningham A L, Tarkowski A, van Rooijen N, Fraser R J, Mahalingam S. 2008. Macrophage-derived proinflammatory factors contribute to the development of arthritis and myositis after infection with an arthrogenic alphavirus. J Infect Dis 197:1585-1593.
30. Chen W, Foo S S, Taylor A, Lulla A, Merits A, Hueston L, Forwood M R, Walsh N C, Sims N A, Herrero L J, Mahalingam S. 2015. Bindarit, an inhibitor of monocyte chemotactic proteins (MCPs) synthesis, protects against bone loss induced by Chikungunya virus infection. J Virol 89:581-593.
31. Chen W, Foo S S, Rulli N, Taylor A, Sheng K C, Herrero L J, Herring B L, Lidbury B A, Li R W, Walsh N C, Sims N A, Smith P N, Mahalingam S. 2014. Arthritogenic alphaviral infection perturbs osteoblast function and triggers pathologic bone loss. Proc Natl Acad Sci USA 111:6040-6045.
32. Chen W, Foo S-S, Sims N A, Herrero L J, Walsh N C, Mahalingam S. 2015. Arthritogenic alphaviruses: new insights into arthritis and bone pathology. Trends in Microbiology 23:35-43.
33. Mann C J, Perdiguero E, Kharraz Y, Aguilar S, Pessina P, Serrano A L, Munoz-Canoves P. 2011. Aberrant repair and fibrosis development in skeletal muscle. Skelet Muscle 1:21.
34. Morrison T E, Fraser R J, Smith P N, Mahalingam S, Heise M T. 2007. Complement contributes to inflammatory tissue destruction in a mouse model of Ross River virus-induced disease. J Virol 81:5132-5143.
35. Ma Y, Pope R M. 2005. The role of macrophages in rheumatoid arthritis. Current pharmaceutical design 11:569-580.
36. Poo Y S, Nakaya H, Gardner J, Larcher T, Schroder W A, Le T T, Major L D, Suhrbier A. 2014. CCR2 Deficiency Promotes Exacerbated Chronic Erosive Neutrophil-Dominated Chikungunya Virus Arthritis. J Virol 88:6862-6872.
37. Bertozzi C R, Freeze H H, Varki A, Esko J D. 2009. Glycans in Biotechnology and the Pharmaceutical Industry. In Varki A. Cummings R D, Esko J D (ed.), Essentials of Glycobiology, 2010 Mar. 20 ed. Cold Spring Harbor (N.Y.).
38. Varki A. 2007. Glycan-based interactions involving vertebrate sialic-acid-recognizing proteins. Nature 446:1023-1029.
39. Nickel J C, Barkin J, Forrest J, Mosbaugh P G, Hernandez-Graulau J, Kaufman D, Lloyd K, Evans R J, Parsons C L, Atkinson L E. 2005. Randomized, double-blind, dose-ranging study of pentosan polysulfate sodium for interstitial cystitis. Urology 65:654-658,
40. Maffrand J P, Herbert J M, Bernat A, Defreyn G, Delebassee D, Savi P, Pinot J J, Sampol J. 1991. Experimental and clinical pharmacology of pentosan polysulfate. Semin Thromb Hemost 17 Suppl 2:186-198.
41. Wu J, Guan T J, Zheng S, Grosjean F, Liu W, Xiong H, Cordon R, Vlassara H, Striker G E, Zheng F. 2011. Inhibition of inflammation by pentosan polysulfate impedes the development and progression of severe diabetic ephropathy in aging C57B6 mice. Lab Invest 91:1459-1471.
42. Stoermer K A, Barrack A, Oko L, Montgomery S A, Borst L B, Gill R G, Morrison T E. 2012. Genetic ablation of arginase 1 in macrophages and neutrophils enhances clearance of an arthritogenic alphavirus. J Immunol 189:4047-4059.
43. Deng B, Wehling-Henricks M, Villalta S A, Wang Y, Tidball J G. 2012. IL-10 triggers changes in macrophage phenotype that promote muscle growth and regeneration. J Immunol 189:3669-3680.
44. Arnold L, Henry A, Poron F, Baba-Amer Y, van Rooijen N, Plonquet A, Gherardi R K, Chazaud B. 2007. Inflammatory monocytes recruited after skeletal muscle injury switch into antiinflammatory macrophages to support myogenesis. J Exp Med 204:1057-1069.

45. Couper K N, Blount D G, Riley E M. 2008. IL-10: the master regulator of immunity to infection. J Immunol 180:5771-5777.
46. Kilgore K S, Naylor K B, Tanhehco E J, Park J L, Booth E A, Washington R A, Lucchesi B R. 1998. The semi-synthetic polysaccharide pentosan polysulfate prevents complement-mediated myocardial injury in the rabbit perfused heart. J Pharmacol Exp Ther 285:987-994.
47. Smith M M, Ghosh P, Numata Y, Bansal M K. 1994. The effects of orally administered calcium pentosan polysulfate on inflammation and cartilage degradation produced in rabbit joints by intraarticular injection of a hyaluronate-polylysine complex. Arthritis Rheum 37:125-136.
48. Morrison N A, Day C J, Nicholson G C. 2014. Dominant negative MCF-1 blocks human osteoclast differentiation. J Cell Biochem 115:303-312.
49. Takizawa M, Yatahe T, Okada A, Chijiiwa M, Mochizuki S, Ghosh P, Okada Y. 2008. Calcium pentosan polysulfate directly inhibits enzymatic activity of ADAMTS4 (aggre-canase-1) in osteoarthritic chondrocytes. FEBS Lett 582: 2945-2949.
50. Ghosh P, Wu J, Shimmon S, Zannettino A C, Gronthos S, Itescu S. 2010. Pentosan polysulfate promotes proliferation and chondrogenic differentiation of adult human bone marrow-derived mesenchymal precursor cells. Arthritis Res Ther 12:R28.
51. Kramer C M, Tsang A S, Koenig T, Jeffcott L B, Dart C M, Dart A J. 2014. Survey of the therapeutic approach and efficacy of pentosan polysulfate for the prevention and treatment of equine osteoarthritis in veterinary practice in Australia. Aust Vet J 92:482-487.
52. Troeberg L, Fushimi K, Khokha R, Emonard H, Ghosh P, Nagase H. 2008. Calcium pentosan poly/sulfate is a multifaceted exosite inhibitor of aggrecanases. FASEB J 22:3515-3524.
53. Al-Zahrani A A, Gajewski J B. 2011. Long-term efficacy and tolerability of pentosan polysulphate sodium in the treatment of bladder pain syndrome. Canadian Urological Association journal=Journal de l'Association des urologues du Canada 5:113-118.
54. Banos S, Bernard M P, Topham D J, Phipps R P. 2009. Ibuprofen and other widely used non-steroidal anti-inflammatory drugs inhibit antibody production in human cells. Cell Immunol 258:18-28.
55. Rulli N E, Guglielmotti A, Mangano G, Rolph M S, Apicella C, Zaid A, Suhrbier A, Mahalingam S. 2009. Amelioration of alphavirus-induced arthritis and myositis in a mouse model by treatment with bindarit, an inhibitor of monocyte chemotactic proteins. Arthritis Rheum 60:2513-2523.
56. Zaid A, Sheng K C, Taylor A, Rulli N E, Herrero L J, McNeil P, Mahalingam S. 2013. Exacerbation of Alphaviral Arthritis and Myositis in a Mouse Model after Etanercept Treatment is due to Diminished Levels of Interferon a/b. Virol Mycol 2:122.
57. Taylor A, Sheng K C, Herrero L J, Chen W, Rulli N E, Mahalingam S. 2013. Methotrexate treatment causes early onset of disease in a mouse model of Ross River virus-induced inflammatory disease through increased monocyte production. PLoS One 8:e71146.

The invention claimed is:

1. A method of treating a subject in need thereof having an alphavirus infection selected from the group consisting of Ross River virus and Chikungunya virus comprising administering parenterally by intra-articular or intra-muscular injection an amount of pentosan polysulfate or a pharmaceutically acceptable salt thereof effective to reduce alphavirus induced inflammation and/or alphavirus induced cartilage damage in a joint of the subject without affecting the viral clearance in the joint or muscle.

2. The method of claim 1 wherein the virus is Ross River virus.

3. The method of claim 1 wherein the virus is chikungunya virus.

4. The method of claim 1 wherein administration is intra-articular.

5. The method of claim 1 wherein administration is intra-muscular.

6. The method of claim 1 wherein the pentosan polysulfate is in the form of its sodium salt.

7. The method of claim 1 wherein administration is daily.

8. The method of claim 1 wherein administration is twice daily.

9. The method of claim 7 wherein the amount administered is within the range of from 0.5 to 5.0 mg/kg body weight of subject.

10. The method of claim 9 wherein the amount is within the range of from 1.0 to 5.0 mg/kg body weight of subject.

11. The method of claim 10 wherein the amount is within the range of from 2.0 to 5.0 mg/kg body weight of subject.

12. The method of claim 11 wherein the subject is a human.

13. The method of claim 1 wherein the subject is a human.

* * * * *

SEQUENCE LISTING

```
<160> NUMBER OF SEQ ID NOS: 12

<210> SEQ ID NO 1
<211> LENGTH: 22
<212> TYPE: DNA
<213> ORGANISM: Homo sapiens

<400> SEQUENCE: 1
caacgccatc tatgagaaaa cc                                              22

<210> SEQ ID NO 2
<211> LENGTH: 21
<212> TYPE: DNA
<213> ORGANISM: Homo sapiens

<400> SEQUENCE: 2
gcccaagaac agtacaatgg t                                               21

<210> SEQ ID NO 3
<211> LENGTH: 23
<212> TYPE: DNA
<213> ORGANISM: Homo sapiens

<400> SEQUENCE: 3
cagaacatca cctaccactg caa                                             23

<210> SEQ ID NO 4
<211> LENGTH: 20
<212> TYPE: DNA
<213> ORGANISM: Homo sapiens

<400> SEQUENCE: 4
```

-continued agaacagcat cgcctacctg                                                           20

<210> SEQ ID NO 5
<211> LENGTH: 24
<212> TYPE: DNA
<213> ORGANISM: Homo sapiens

<400> SEQUENCE: 5
agcaggctgc agttctcaga cagc                                                      24

<210> SEQ ID NO 6
<211> LENGTH: 25
<212> TYPE: DNA
<213> ORGANISM: Homo sapiens

<400> SEQUENCE: 6
cactgacttc ctggacaatg gttat                                                     25

<210> SEQ ID NO 7
<211> LENGTH: 23
<212> TYPE: DNA
<213> ORGANISM: Homo sapiens

<400> SEQUENCE: 7
gatgatcagg aagaggacta cga                                                       23

<210> SEQ ID NO 8
<211> LENGTH: 20
<212> TYPE: DNA
<213> ORGANISM: Homo sapiens

<400> SEQUENCE: 8
tggagctgat gcataagccc                                                           20

<210> SEQ ID NO 9
<211> LENGTH: 22
<212> TYPE: DNA
<213> ORGANISM: Homo sapiens

<400> SEQUENCE: 9
ggaactcaca cgacatcttc ca                                                        22

<210> SEQ ID NO 10
<211> LENGTH: 26
<212> TYPE: DNA
<213> ORGANISM: Homo sapiens

<400> SEQUENCE: 10
ggcactctgg tctacactat taagca                                                    26

<210> SEQ ID NO 11
<211> LENGTH: 20
<212> TYPE: DNA
<213> ORGANISM: Homo sapiens

<400> SEQUENCE: 11
ccgtggcggg tattatcaat                                                           20

-continued

```
<210> SEQ ID NO 12
<211> LENGTH: 19
<212> TYPE: DNA
<213> ORGANISM: Homo sapiens

<400> SEQUENCE: 12
attaagagtg tagccatcc                                                     19
```